(12) United States Patent
Bose et al.

(10) Patent No.: US 9,539,359 B2
(45) Date of Patent: *Jan. 10, 2017

(54) MESOPOROUS CALCIUM SILICATE COMPOSITIONS AND METHODS FOR SYNTHESIS OF MESOPOROUS CALCIUM SILICATE FOR CONTROLLED RELEASE OF BIOACTIVE AGENTS

(71) Applicant: Washington State University, Pullman, WA (US)

(72) Inventors: Susmita Bose, Pullman, WA (US); Amit Bandyopadhyay, Pullman, WA (US); Weichang Xue, Suzhou (CN)

(73) Assignee: Washington State University, Pullman, WA (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/538,418

(22) Filed: Nov. 11, 2014

(65) Prior Publication Data

US 2015/0283294 A1   Oct. 8, 2015

Related U.S. Application Data

(62) Division of application No. 12/211,005, filed on Sep. 15, 2008, now Pat. No. 8,916,198.

(60) Provisional application No. 60/972,619, filed on Sep. 14, 2007.

(51) Int. Cl.
| | |
|---|---|
| A61L 27/02 | (2006.01) |
| A61L 27/10 | (2006.01) |
| A61L 27/22 | (2006.01) |
| A61L 27/54 | (2006.01) |
| A61L 27/56 | (2006.01) |
| A61L 27/28 | (2006.01) |
| A61K 9/51 | (2006.01) |
| A61K 47/48 | (2006.01) |
| A61L 27/30 | (2006.01) |
| A61L 27/58 | (2006.01) |

(52) U.S. Cl.
CPC ............ *A61L 27/025* (2013.01); *A61K 9/5115* (2013.01); *A61K 47/48861* (2013.01); *A61L 27/10* (2013.01); *A61L 27/227* (2013.01); *A61L 27/306* (2013.01); *A61L 27/54* (2013.01); *A61L 27/56* (2013.01); *A61L 27/58* (2013.01); *A61L 2300/252* (2013.01); *A61L 2300/254* (2013.01); *A61L 2300/414* (2013.01); *A61L 2300/428* (2013.01); *A61L 2300/45* (2013.01); *A61L 2300/602* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,718,914 A | 1/1988 | Frey |
| 5,026,591 A | 6/1991 | Henn et al. |
| 5,032,552 A | 7/1991 | Nonami et al. |
| 5,246,530 A | 9/1993 | Bugle et al. |
| 5,338,772 A | 8/1994 | Bauer et al. |
| 5,484,286 A | 1/1996 | Hansson |
| 5,843,172 A | 12/1998 | Yan |
| 6,013,591 A | 1/2000 | Ying |
| 6,471,993 B1 | 10/2002 | Shastri et al. |
| 6,689,170 B1 | 2/2004 | Larsson et al. |
| 6,790,233 B2 | 9/2004 | Brodke et al. |
| 7,048,541 B2 | 5/2006 | Hall et al. |
| 2002/0062154 A1 | 5/2002 | Ayers |
| 2002/0173850 A1 | 11/2002 | Brodke et al. |
| 2003/0193106 A1 | 10/2003 | Yu et al. |
| 2004/0019385 A1 | 1/2004 | Ayers et al. |
| 2004/0023784 A1 | 2/2004 | Yu et al. |
| 2004/0082999 A1 | 4/2004 | Mathys, Jr. et al. |
| 2004/0101822 A1 | 5/2004 | Wiesner et al. |
| 2004/0142013 A1 | 7/2004 | Rubsamen |
| 2004/0243237 A1 | 12/2004 | Unwin et al. |

(Continued)

FOREIGN PATENT DOCUMENTS

| | | |
|---|---|---|
| EP | 1440669 | 2/2003 |
| EP | 1449544 | 8/2004 |

(Continued)

OTHER PUBLICATIONS

Zerbo, et al., "Histomorphometry of human sinus floor augmentation using a porous 13-tricalcium phosphate: a prospective study," Clinical ora/Implant Research (2004) 15.

(Continued)

*Primary Examiner* — Susan Tran
*Assistant Examiner* — William Craigo
(74) *Attorney, Agent, or Firm* — Liang IP, PLLC

(57) ABSTRACT

Mesoporous calcium silicate compositions for controlled release of bioactive agents and methods for producing such compositions are disclosed herein. In one embodiment, mesoporous calcium silicate is synthesized by acid modification of wollastonite particles using hydrochloric acid. A hydrated silica gel layer having abundant Si—OH functional groups can be formed on the surface of wollastonite after acid modification. Bruhauer-Emmett-Teller (BET) surface area increased significantly due to acid modification and, in one arrangement, reached over 350 $m^2/g$. Acid modified mesoporous calcium silicate compositions show a higher ability to adsorb protein compared to unmodified particles and demonstrate controlled release kinetics of these proteins.

19 Claims, 13 Drawing Sheets

(56) References Cited

U.S. PATENT DOCUMENTS

| | | |
|---|---|---|
| 2004/0254668 A1 | 12/2004 | Jang et al. |
| 2005/0221072 A1 | 10/2005 | Dubrow et al. |
| 2006/0078590 A1* | 4/2006 | Hermansson ............ A61L 27/12 424/426 |
| 2006/0188542 A1 | 8/2006 | Bobyn et al. |
| 2006/0229715 A1 | 10/2006 | Istephanous et al. |
| 2007/0098811 A1 | 5/2007 | Lu et al. |
| 2007/0203584 A1 | 8/2007 | Bandyopadhyay et al. |
| 2009/0276056 A1 | 11/2009 | Bose |

FOREIGN PATENT DOCUMENTS

| | | |
|---|---|---|
| WO | WO9511639 | 5/1995 |
| WO | WO9966966 | 12/1999 |
| WO | WO0072777 | 12/2000 |
| WO | WO2004008984 | 1/2004 |
| WO | WO2005000159 | 1/2005 |
| WO | WO2006116752 | 11/2006 |
| WO | WO-2007124511 | 11/2007 |

OTHER PUBLICATIONS

Zerbo, et al., Histology of human alveolar bone regeneration with a porous tricalcium phosphate. A report of two cases. Clin Ora/ Implants Res. 12:379-384 (2001).

Zhang, et al., "Crystallization and microstructure analysis of calcium phosphate-based glass ceramics for biomedical applications," J. of Non-Crystalline Solids, 272 (2000) 14-21.

Bhadang, et al., "Influence of fluorapatite on the properties of thermally sprayed hydroxyapatite coatings," Biomaterials 25 (2004) 4935-4945.

Gibson, et al., "Phase Transformation of Tricalcium Phosphates Using High Temperature X-Ray Diffraction," Bioceramics vol. 9, 173-176 (1996).

Heughebaert, et al., "Physicochemical Characterization of Deposits Associated with HA Ceramics Implanted in Nonosseous Sites," J. Biomed. Mater. Res.: Applied Biomaterials (1988) 22:A3, pp. 257-268.

Kawamura, et al., "Stimulatory effect of zinc-releasing calcium phosphate implant on bone formation in rabbit femora", J. Biomed. Mater. Res., 50 f21184-190 (2000).

Legeros, et al., "In Vivo Transformation of Biphasic Calcium Phosphate Ceramics: Ultrastructural and Physicochemical Characterizations," In: CRC Handbook of Bioactive Ceramics vol. II Calcium Phosphate and Hydroxylapatite Ceramics, Yamanuro T, Hench L, Wilson J, editors. Boca Raton: CRC Press, 1990, vol. 2, pp. 17-28.

Legeros, et al., "The effect of magnesium on the formation of apatites and whitlockites," In: Magnesium in Health and Disease, Y. Itokawa & J. Durlach, eds., London: John Libbey & Co Ltd.; 11 (1989), pp. 11-19.

Moreira-Gonzalez, et al., "Evaluation of 45S5 Bioactive Glass Combined as a Bone Substitute in the Reconstruction of Critical Size Calvarial Defects in Rabbits," The J. Craniofac. Surg., Jan. 2005, vol. 16, No. 1, pp. 63-70.

Mow, et al., Basic Orthopaedic Biomechanics and Mechano-Biology, Third Edition, pp. 123-519, Lippencott Williams & Wilkins, Philadelphia, 2005.

Oki, et al., "Preparation and in vitro bioactivity of zinc containing sol-gel-derived bioglass materials," J. Biomed. Mater. Res. 69A:216-221 (2004).

Shi, Biomaterials and Tissue Engineerinq, pp. 1-215, Spriner Berlin Heidelber, New York, 2004.

Vandenburgh, et al., "Mechanically induced alterations in cultured skeletal muscle growth," J. Biomech. (1991)24: Suppl. 1, pp. 91-99.

Yin, et al., "Density Functional Study of Structural, Electronic and Vibrational properties of Mg- and Zn-doped Tricalcium Phosphate Biomaterials", Biomaterials, 23 [20] 4155-4163 (2002).

Zhang, et al., "A Comparative Study of Electrochemical Deposition and Biomimetic Deposition of Calcium Phosphate on porous Titanium", Biomaterials; 26 f16]2857-2865 (2005).

Y. I. Zawahreh. Effects of Ti02, Zr02 and A1203 dopants on the compressive strength of tricalcium phosphate (2005) Journal of Materials Science.

S. Yoshihara. Effects of glass composition on compressive strength of bioactive cement based on Ca0-Si02-P205 glass powders. (1993). Journal of Materials Science.

Office Action in U.S. Appl. No. 12/298,012 issued Feb. 28, 2013, 13 pages.

Office Action in U.S. Appl. No. 12/298,012 issued Nov. 7, 2013, 17 pages.

Office Action in U.S. Appl. No. 12/298,012 issued Feb. 23, 2014, 22 pages.

Office Action in U.S. Appl. No. 11/675,006 issued Jul. 28, 2009, 6 pages.

Office Action in U.S. Appl. No. 11/675,006 issued May 10, 2010, 8 pages.

Office Action in U.S. Appl. No. 11/675,006 issued May 15, 2013, 9 pages.

Office Action in U.S. Appl. No. 11/675,006 issued Feb. 12, 2014, 8 pages.

Office Action in U.S. Appl. No. 12/298,012 issued Aug. 18, 2014, 15 pages.

Borden et al. The sintered microsphere matrix for bone tissue engineering: In vitro osteoconductivity studies. 2002. Wiley Periodicals, Inc. pp. 421-429.

Gomes et al. Biodegradable polymers and composites in biomedical applications: from catgut to tissue engineering. 2004. Maney for the Institute and ASM International. vol. 49. No. 5. pp. 261-273.

Saravanapavan, Journal of Non-Crystalline Solids, 318, pp. 1-13, 2003.

Saravanapavan, Journal of Non-Crystalline Solids, 318, pp. 14-26, 2003.

Saravanapavan, Bio-Medical Materials and Engineering, 14, 2004.

Bandyopadhyay, et al., "Calcium Phosphate-Based Resorbable Ceramics: Influence of MgO, ZnO, and Si02 Dopants," J. Am. Ceram. Soc., 89 [9], pp. 2675-2688 (2006).

Bandyopadhyay, et al., "Influence of ZnO doping in calcium phosphate ceramics", in press, Materials Science and Engineering C, Nov. 2005.

Bertoni, et al., "Nanocrystals of Magnesium and fluoride substituted hydroxyapatite". J. lnorg. Biochem., 72, 29-35 (1998).

Bose, et al., ""Synthesis and characterization of hydroxyapatite nanopowders by emulsiontechnique,"" Chern Mater., 15 (23), 4464-4469 (2003).

Bose, et al., "Synthesis of hydroxyapatite nanopowders via sucrose-templated sol-gel method," Journal of the American Ceramic Society, 86 [6], pp. 1055-1057 (2003).

Bose, et al., "Pore Size and Pore Volume Effects on Alumina and TCP Ceramic Scaffolds," Materials Science and Engineerinq C, 23, pp. 479-486 (2003).

Burg, et al., "Biomaterial developments for bone tissue engineering". Biomaterials, 21 [23]2347-59 (2000).

Buser, et al., "Localized ridge augmentation using guided bone regeneration"; pp. 189-233 in Guided bone regeneration in implant dentistry, Edited by D. Buser, C. Dahlin and R. K. Schenk, Quintessenz, Chicaqo, 1994.

De Groot, "Effect of porosity and physicochemical properties on the stability, resorption, and strength of calcium phosphate ceramics". In Bioceramics: Material characteristics versus in-vivo behavior, Ann. N.Y. Acad. Sci., 523,227 (1998).

Doi, et al., "Development of a new calcium phosphate cement that contains sodium calcium phosphate," Biomaterials 22 (2001) 847-845.

Ducheyne, et al., "Bioactive ceramics: the effect of surface reactivity on bone formation and bone cell function," Biomaterials (1999) 20:23-24, pp. 2287-2303.

Fujimura, et al., "A bioactive bone cement containing Bis-GMA resin and A-W glass-ceramic as an augmentation graft material on mandibular bone," Clin Ora/Implants Res (2003) 14, pp. 659-667.

(56) References Cited

OTHER PUBLICATIONS

Hashizume, et al., "Stimulatory effect of 133-alanyl-1-histidinato zinc on cell proliferation is dependent on protein synthesis in osteoblastic MC3T3-E1 cells", Mol. Cell Biochem., 122, 59-64 (1993).
Hattiangadi, et al., "Strength Degradation of Nonrandom Porous Ceramics Under Uniaxial Compressive Loading," Journal of the American Ceramic Society, 83 [11], pp. 2730-2736 (2000).
Hayakawa, et al., "Mechanism of apatite formation on a sodium glass in a simulated body fluid", J. Am. Ceram. Soc., 82 f812155-60 (1999).
Hulbert, et al. Potential of ceramic materials as permanently implantable skeletal prosthesis. J Biomed Mater Res 1970; 4:443.
Inoue, et al., "In vivo effect of fluoride-substituted apatite on rat bone," Dent Mater J. Sep. 2005; 24 (3); 398.
Ito, et al., "Preparation, solubility, and cytocompatibility of zinc-releasing calcium phosphate ceramics", J. Biomed. Mater. Res., 50 [2]178-183 (2000).
Josch E K, et al., Chemical and physicochemical characterization of porous hydroxyapatite ceramics made of natural bone. Biomaterals. 21:1645-1658 (2000).
Kalita, et al., "Development of controlled porosity polymer-ceramic composite scaffolds via fused deposition modelinq," Materials Science and Enqineerinq C 23:611-620 (2003).
Kalita, et al., "Effects of Mg0-Ca0-P20 5-Na20 based additives on mechanical and biological properties of hydroxyapatite," in press, Journal of Biomedical Materials Research, Jun. 2004.
Kalita, et al., "CaO-P20s-Na20 based sintering additives for hydroxyapatite (HAp) ceramics," Biomaterials, 25:12, pp. 2331-2339 (2004).
Kamakura, et al., Implanted octacalcium phosphate is more resorbable than 13-tricalcium phosphate and hydroxyapatite. J Biomed Mater Res. 59:29-34 (2002).
Kim, et al., "Synthesis of Si, Mg substituted hydroxyapatites and their sintering behaviors", Biomaterials. 24 f81 1389-98 (2003).
Kishi, et al., "Inhibitory effect of zinc compounds on osteoclast-like cell formation in mouse marrow culture", Biochem. Pharmacal., 48, 1225-1230 (1994).
Knabe, et al., Effect of rapidly resorbable calcium phosphates and a calcium phosphate bone cement on the expression of bone-related genes and proteins in vitro, J Biomed Mater Res. 69A: 145-154 15 (2004).
Knabe, et al., "The functional expression of human bone-derived cells grown on rapidly resorbable calcium phosphate ceramics", Biomaterials. 25 [2] 335-44 (2004).
Knowles, et al., "Sintering effects in a glass reinforced hydroxyapatite", Biomaterials, 17 [14] 1437 (1996).
Kokubo, et al., "Solutions able to reproduce in vivo surface-structure changes in bioactive glassceramicA-W3", J. Biomed. Mater. Res., 24,721-34 (1990).
Lansdown, Silver 2: toxicity in mammals and how its products aid wound repair 11, 173 (2002).
Larrabee, et al., A ferric calcium phosphorous oxide (FE CAP) ceramic for rebuilding bone. Biomed Sci Instrurn. 29:59-64 (1993).
Leng, et al., "Identifying Calcium Phosphates Formed in Simulated Body Fluid by Electron Diffraction", Hey. Eng. Mater., 254 [25]339-42 (2004).
Manjubala, et al., Effect of Ti02Ag20 additives on the formation of calcium phosphate based functionally qraded bioceramics. Biomaterials. 21:1995-2002 (2000).
Marcacci, et al., "Reconstruction of extensive long-bone defects in sheep using porous hydroxyapatite sponges," Calcif Tissue Int (1999) 64, pp. 83-90.
Moonga, et al., "Zinc is a potent inhibitor of osteoclastic bone resorption in vitro", J. Bone Miner. Res., 10 [3]453-457 (1995).
Moritz, et al., "Local induction of calcium phosphate formation on Ti02 coatings on titanium via surface treatment with a C02 laser," J of biomed mater res A, 65 (2003) 9-16.

Otsuka, et al., Effect of controlled zinc release on bone mineral density from injectable Zncontaining 13-tricalcium phosphate suspension in zinc-deficient diseased rats. J Biomed Mater Res. 69A:552-560 (2004).
Percival, "Bone health & Osteoporosis", Appl. Nutr. Sci. Rep., 5 [4]1 (1999).
Qiu, et al., "Effect of strontium ions on the growth of ROS17 /2.8 cells on porous calcium polyphosphate scaffolds", Biomaterials; 27 f811277-86 (2006).
Ramires, et al., "The influence of titania/hydroxyapatite composite coatings on in vitro osteoblasts behaviour," Biomaterials, 22(12):1467-74 (2001).
Rodriguez-Lorenzo, et al., "Influence of fluorine in the synthesis of apatites, synthesis of solid solutions of hydroxyl-fluorapatite," Biomaterials 24 (2003) 3777-3785.
Rokusek, et al., "Interaction of human osteoblasts with bioinert and bioactive ceramic substrates", J. Biomed. Mater. Res., 75A f31588-94 (2005).
Seeley, et al., "Tricalcium phosphate based resorbable ceramics: Influence of NaF and GaO addition," Mater. Sci. Enq. C, vol. 28, Issue 1, pp. 11-17 (2008).
Seeley, et al., "Influence of Ti02 and Ag 20 Addition on Tricalcium Phosphate Ceramics", J. Biomed. Mater. Res., vol. 82A, Issue 1, pp. 113-121, Jul. 2007.
Suchanek, et al., "Processing and Properties of Hydroxyapatite-Based Biomaterials for Use as Hard Tissue Replacement Implants", J. Mater. Res., 13 [1]94-109 (1998).
Tadjoedin, et al., "High concentrations of bioactive glass material (BioGran®) vs. autogenous bone for sinus floor elevation," Clinical Ora/Implants Research (2002) 13:4, pp. 428-436.
Wang, "Ca/P ratio effects on the degradation of hydroxyapatite in vitro," J. of Biomedical Materials Research part A, 67A:2, pp. 599-608.
Yaszemski, et al., "Evolution of bone transplantation: molecular, cellular and tissue strategies to engineer human bone," Biomaterials (1996) 17:2, pp. 175-185.
Yin, et al., "Density Functional Study of Structural, Electronic and Vibrational properties of Mg-and Zn-doped Tricalcium Phosphate Biomaterials", Biomaterials 23 f201 4155-4163 (2002).
Zamir, et al., "Molecular complexity and dynamics of cell-matrix adhesions", J. Cell Sci. 114 [20] 3583-90 (2001).
Anderson, J.M. et al. "Biodegradation and biocompatibility of PLA and PLGA microspheres," Advanced Drug Delivery Reviews 28 (1997) 5-24.
Andreadis, S.T. et al. "Biomimetic approaches to protein and gene delivery for tissue regeneration," Trends in Biotechnology 24 (2006) 331-337.
Angeli, F. et al. "Influence of glass composition and alteration solution on leached silicate glass structure: A solid-state NMR investigation," Geochimica et Cosmochimica Acta 70 (2006) 2577-2590.
Balas, F. et al., "L-Trp adsorption into silica mesoporous materials to promote bone formation," Acta Biomaterialia 4 (2008) 514-522.
Baldwin, S.P. et al. "Materials for protein delivery in tissue engineering," Advanced Drug Delivery Reviews 33 (1998) 71-86.
Barbe, C. et al. "Silica Particles: A Novel Drug-Delivery System," Adv. Mater. 16 (2004) 1959-1966.
Blom, E.J. et al. "Transforming growth factor-β1 incorporation in an α-tricalcium phosphate/dicalcium phosphate dihydrate/ tetracalcium phosphate monoxide cement: release characteristics and physiochemical properties," Biomaterials 23 (2002) 1261-1268.
Casey, W.H. et al. "Leaching and reconstruction at the surfaces of dissolving chain-silicate minerals," Nature 366 (1993) 253-256.
Chen, J.J. et al. "Solubility and structure of calcium silicate hydrate," Cement and Concrete Research 34 (2004) 1499-1519.
De Aza, P.N. et al. "Bioactivity of Wollastonite Ceramics: In Vitro Evaluation," Scripta Metallurgica et Materialia 31 (1994) 1001-1005.
De Aza, P.N. et al. "Morphological and structural study of pseudowallastonite implants in bone," Journal of Microscopy 197 (2000) 60-67.

(56) References Cited

OTHER PUBLICATIONS

Ginebra, M.-P. et al. "Calcium phosphate cements: Competitive drug carriers for the musculoskeletal system?," Biomaterials 27 (2006) 2171-2177.
Haesslein, A. et al. "Effect of macromer molecular weight on in vitro ophthalmic drug release from photo-crosslinked matrices," Acta Biomaterialia 4 (2008) 1-10.
Hartmann, M. "Ordered Mesoporous Materials for Bioadsorption and Biocatalysis," Chem. Mater. 17 (2005) 4577-4593.
Hartmann, M. et al. "Adsorption of Vitamin E on Mesoporous Carbon Molecular Sieves," Chem. Mater. 17 (2005) 829-833.
Hench, L.L. "Bioceramics: From Concept to Clinic," J. Am. Ceram. Soc. 74 (1991) 1487-1510.
Holland, T.A. et al. "Advances in drug delivery for articular cartilage," Journal of Controlled Release 86 (2003) 1-14.
Horcajada, P. et al. "Bioactivity in ordered mesoporous materials," Solid State Sciences 6 (2004) 1295-1300.
Kokubo, T. "Novel bioactive materials with different mechanical properties," Biomaterials 24 (2003) 2161-2175.
Kumta, P.N. et al. "Nanostructured calcium phosphates for biomedical applications: novel synthesis and characterization," Acta Biomaterialia 1 (2005) 65-83.
Lee, J.Y. et al. "Transforming Growth Factor (TGF)-β1 Releasing Tricalcium Phosphate/Chitosan Microgranules as Bone Substitutes," Pharmaceutical Research 21 (2004) 1790-1796.
Li, P. et al. "The Electrochemistry of a Glass Surface and its Application to Bioactive Glass in Solution," Journal of Non-Crystalline Solids 119 (1990) 112-118.
Lin, K. et al. "Study of the mechanical property and in vitro biocompatibility of $CaSiO_3$ ceramics," Ceramics International 31 (2005) 323-326.
Liong, M. et al. "Multifunctional Inorganic Nanoparticles for Imaging, Targeting, and Drug Delivery," ACS Nano 2 (2008) 889-896.
Liu, X. et al. "Apatite formed on the surface of plasma-sprayed wollastonite coating immersed in simulated body fluid," Biomaterials 22 (2001) 2007-2012.
Luginbuehl, V. et al. "Localized delivery of growth factors for bone repair," European Journal of Pharmaceutics and Biopharmaceutics 58 (2004) 197-208.
Melillo, M. et al. "Structural Characteristics of Activated Carbons and Ibuprofen Adsorption Affected by Bovine Serum Albumin," Langmuir 20 (2004) 2837-2851.
Olton, D. et al. "Nanostructured calcium phosphates (NanoCaPs) for non-viral gene delivery: Influence of the synthesis parameters on transfection efficiency," Biomaterials 28 (2007) 1267-1279.
Panyam, J. et al. "Biodegradable nanoparticles for drug and gene delivery to cells and tissue," Advanced Drug Delivery Reviews 55 (2003) 329-347.
Parida, S.K. et al. "Adsorption of organic molecules on silica surface," Advances in Colloid and Interface Science 121 (2006) 77-110.
Rai, B. et al. "Novel PCL-based honeycomb scaffolds as drug delivery systems for rhBMP-2," Biomaterials 26 (2005) 3739-3748.
Sahai, N. et al. "Molecular Orbital Study of Apatite ($Ca_5(PO_4)_3OH$) Nucleation at Silica Bioceramic Surfaces," J. Phys. Chem. B 104 (2000) 4322-4341.
Schmidt, H.T. et al. "Assembly of Aqueous-Cored Calcium Phosphate Nanoparticles for Drug Delivery," Chem. Mater. 2004, 16, 4942-4947.
Schmidt, S.M. et al. "Surfactant based assembly of mesoporous patterned calcium phosphate micron-sized rods," Microporous and Mesoporous Materials 94 (2006) 330-338.
Seeherman, H. et al. "Delivery of bone morphogenetic proteins for orthopedic tissue regeneration," Cytokine & Growth Factor Reviews 16 (2005) 329-345.
Slowing, I.I. et al. "Mesoporous Silica Nanoparticles for Drug Delivery and Biosensing Applications," Adv. Funct. Mater. 17 (2007) 1225-1236.
Vallet-Regi, M. et al. "A New Property of MCM-41: Drug Delivery System," Chem. Mater. 13 (2001) 308-311.
Wan, X. et al. "Preparation and in vitro bioactivities of calcium silicate nanophase materials," Materials Science and Engineering C 25 (2005) 455-461.
Weissbart, E.J. et al. "Wallastonite: Incongruent dissolution and leached layer formation," Geochimica et Cosmochimica Acta 64 (2000) 4007-4016.
Xia, W. et al. "Well-ordered mesoporous bioactive glasses (MBG): A promising bioactive drug delivery system," Journal of Controlled Release 110 (2006) 522-530.
Xu, Z.P. et al. "Inorganic nanoparticles as carriers for efficient cellular delivery," Chemical Engineering Science 61 (2006) 1027-1040.
Xue, W. et al. "In vivo evaluation of plasma-sprayed wollastonite coating," Biomaterials 26 (2005) 3455-3460.
Notice of Allowance in U.S. Appl. No. 12/298,012 issued Jan. 14, 2015, 12 pages.
Office Action in U.S. Appl. No. 14/682,343 issued Nov. 13, 2015, 16 pages.
Notice of Allowance in U.S. Appl. No. 11/675,006 issued Jan. 14, 2016, 9 pages.
Office Action in U.S. Appl. No. 14/682,343 issued May 5, 2016, 16 pages.
Camire et al., "Material characterization and in vivo behavior of silicon substituted alpha-tricalcium phosphate cement," Sep. 23, 2005.
Office Action in U.S. Appl. No. 14/682,343 issued Aug. 25, 2016, 19 pages.

* cited by examiner

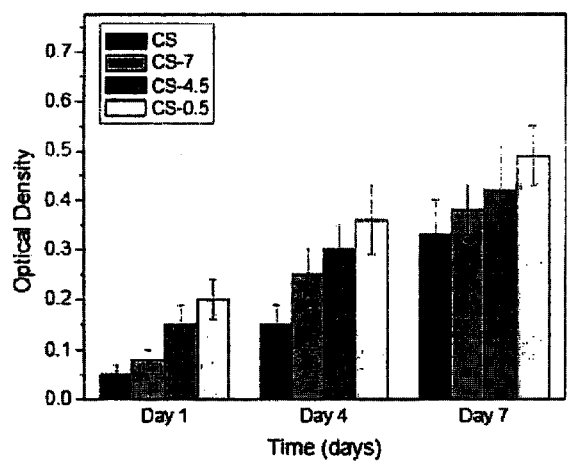
FIG. 13
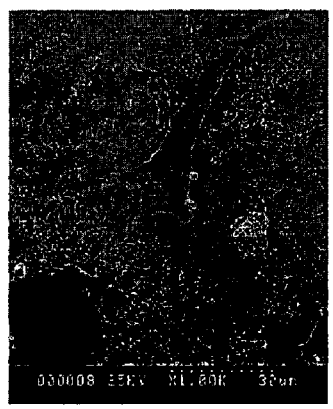 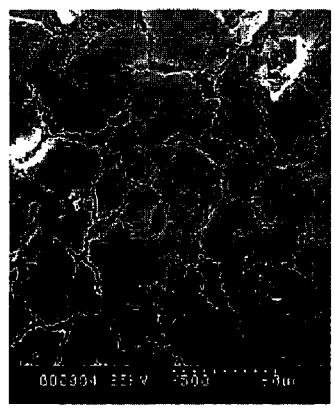
FIG. 14A     FIG. 14B

MESOPOROUS CALCIUM SILICATE COMPOSITIONS AND METHODS FOR SYNTHESIS OF MESOPOROUS CALCIUM SILICATE FOR CONTROLLED RELEASE OF BIOACTIVE AGENTS

CROSS-REFERENCE TO APPLICATION(S) INCORPORATED BY REFERENCE

The present application is a divisional application of U.S. patent application Ser. No. 12/211,005, filed Sep. 15, 2008, now U.S. Pat. No. 8,916,198, issued Dec. 23, 2014, which claims priority to U.S. Provisional Patent Application No. 60/972,619, filed Sep. 14, 2007, entitled "METHODS FOR SYNTHESIS OF MESOPOROUS CALCIUM SILICATE FOR CONTROLLED RELEASE OF PROTEIN," and incorporated herein in its entirety by reference. The present application incorporates the subject matter of International Publication No. WO/2007/124511, entitled "RESORBABLE CERAMICS WITH CONTROLLED STRENGTH LOSS RATES," filed Apr. 25, 2007, and U.S. Publication No. 2007/0203584 A1, entitled "BONE REPLACEMENT MATERIALS," filed Feb. 14, 2007, now U.S. Pat. No. 9,327,056, issued on May 3, 2016, in their entirety by reference.

STATEMENT REGARDING FEDERALLY SPONSORED RESEARCH

This invention was made with government support under CTS-0134476 awarded by the National Science Foundation, under N00014-04-1-0644 and N00014-05-1-0583 awarded by the Office of Naval Research, and under R01 EB007351 awarded by National Institute of Biomedical Imaging and Bioengineering of the National Institutes of Health. The government has certain rights in this invention.

TECHNICAL FIELD

The present disclosure is generally directed to mesoporous calcium silicate compositions for use in bone regeneration and other biomedical applications, and directed to synthesis of mesoporous calcium silicate for controlled release of bioactive agents, such as proteins and/or pharmaceutical agents.

BACKGROUND

Bone forming growth factors, such as bone morphogenetic protein (BMP) and transforming growth factor (TGF-β) have been widely investigated in orthopedics and tissue engineering with great success. These molecules stimulate bone cell growth and differentiation, and accelerate bone tissue regeneration [1, 2]. To prevent possible side-effects in non-target tissues, delivery of growth factors are performed in a controlled manner. For example, growth factors can be sequentially administered in a manner that mimics the time profile of the healing process [2-4].

Biomaterials, such as biopolymers [5-8], inorganic ceramics [9-18] and their compositions [19, 20], can act as reservoirs for deliverable protein and other bioactive molecules if they demonstrate a high capacity for protein adsorption while preserving the protein structure and biological activity over time. In addition to controlled protein delivery, carriers that are biocompatible with bone tissue can also serve as a scaffold for new tissue formation during normal tissue repair or healing. Furthermore, such biomaterials should be non-immunogenic and, in many cases, biodegradable once tissue regeneration is complete [2, 3]. Typically, biopolymers are not bioactive because they do not chemically bond to living bone. Inorganic bone replacement materials, including calcium phosphate ceramics [10, 11], bioglass and bioglass-ceramics [12], silica gel [13, 14], and calcium phosphate cements [15-18], have been extensively investigated due to their excellent bioactivity with bone tissue. However, the adsorption capacity of protein on these carriers is limited to outer surface adsorption. Moreover, protein release from these materials displays a burst release (e.g., rapid release) due to the weak bonding between protein and the carriers.

BRIEF DESCRIPTION OF THE DRAWINGS

In order that advantages of the disclosure will be readily understood, a more particular description of aspects of the disclosure briefly described above will be rendered by reference to specific embodiments and the appended drawings. Understanding that these drawings depict only typical embodiments of the disclosure and are not therefore to be considered to be limiting of its scope, the disclosure will be described and explained with additional specificity and detail through the use of the accompanying drawings.

FIGS. 1A-1C illustrate a reaction mechanism of (A) wollastonite chain-silicate structure consisting of a network of covalently bonded silica that is interrupted and modified by Ca cations, (B) a reaction step wherein weakly bonded, network-modifying Ca is released relatively quickly to solution as Ca is exchanged for hydrogen ions and (C) a reaction step wherein silanol (Si—OH) in the leach layer repolymerizes to form a silica gel, and in accordance with an embodiment of the disclosure.

FIG. 2 is a XRD spectra of calcium silicate before and after acid modification in accordance with an embodiment of the disclosure.

FIG. 3 is a FTIR spectra of calcium silicate before and after acid modification in accordance with an embodiment of the disclosure.

FIG. 4 is a $^{29}$Si magic-angle spinning (MAS) nuclear magnetic resonance (NMR) analysis of calcium silicate before (CS) and after (CS-7) acid modification in accordance with an embodiment of the disclosure.

FIGS. 5A-5C are, respectively, SEM images of morphologies and microstructures of calcium silicate after acid treatment at (A) pH 7.0, (B) pH 4.5 and (C) pH 0.5, and in accordance with an embodiment of the disclosure.

FIGS. 6A-6C are, respectively, graphical representations of a size distribution of (A) CS-7 mesoporous calcium silicate, (B) CS-4.5 mesoporous calcium silicate and (C) CS-0.5 mesoporous calcium silicate in accordance with an embodiment of the disclosure.

FIGS. 7A-7B are, respectively, graphical representations of the kinetics of BSA adsorption on calcium silicate and mesoporous calcium silicate at (A) pH 7 and (B) pH 4.5 in accordance with an embodiment of the disclosure.

FIG. 8 is a graphical representation of the kinetics of lysozyme adsorption on calcium silicate and mesoporous calcium silicate in accordance with an embodiment of the disclosure.

FIG. 9 is a FTIR spectra of mesoporous calcium silicate before and following lysozyme adsorption in accordance with an embodiment of the disclosure.

FIG. 10 is a graphical representation of nitrogen adsorption isotherms of mesoporous calcium silicate before and following lysozyme adsorption in accordance with an embodiment of the disclosure.

FIG. 13 is a graphical representation of cell densities of human fetal osteoblast cells cultured with samples of calcium silicate and mesoporous calcium silicate in accordance with an embodiment of the disclosure.

FIGS. 14A-14B are SEM images of morphologies of cells cultured on pressed mesoporous calcium silicate after 3 days (14A) and 7 days (14B) of culture in accordance with an embodiment of the disclosure.

DETAILED DESCRIPTION

Figure 1A:
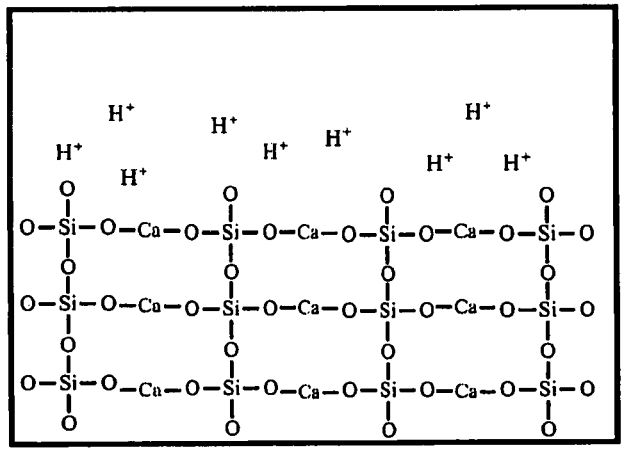

The present disclosure describes mesoporous calcium silicate compositions and methods for producing mesoporous calcium silicate for controlled release of bioactive agents. In some embodiments, bioactive agents can include proteins, growth factors (e.g., osteoinductive growth factors), pharmaceutical drugs, antibiotics, antimicrobial agents, polypeptides, etc. In one embodiment, mesoporous calcium silicate is synthesized by acid modification of wollastonite (e.g., calcium silicate) particles by adding hydrochloric acid to a wollastonite slurry until a neutral (e.g., 7.0) or acidic (less than 7.0) pH level is achieved. A hydrated silica gel layer having abundant Si—OH functional groups can be formed on the surface of calcium silicate particles following acid modification. In further embodiments, acid modification of calcium silicate particles increases particle surface area, as measured by the Bruhauer-Emmett-Teller (BET) method. Acid modified mesoporous calcium silicate particles demonstrate an increased ability to adsorb protein compared to unmodified calcium silicate particles, and further demonstrate controlled release kinetics of these proteins. Accordingly, the compositions disclosed herein provide calcium silicate materials for use in bone implant applications having increased bioactivity and bioactive agent loading.

It will be appreciated that several of the details set forth below are provided to describe the following embodiments in a manner sufficient to enable a person skilled in the relevant art to make and use the disclosed embodiments. Several of the details and advantages described below, however, may not be necessary to practice certain embodiments of the disclosure. Additionally, the disclosure can include other embodiments that are within the scope of the claims but are not described in detail with respect to FIGS. 1A-14B.

A. EMBODIMENTS OF MESOPOROUS CALCIUM SILICATE COMPOSITIONS AND METHODS FOR PREPARING AND USING SUCH COMPOSITIONS

Particular aspects of the present disclosure provide mesoporous calcium silicate compositions for controlled release of bioactive agents to be used for or used with bone replacement materials (e.g., three-dimensional tissue scaffolds). Mesoporous calcium silicate compositions can be used alone or in combination with other biocompatible scaffold materials (e.g., calcium phosphates [CaP] with or without dopants to facilitate controlled strength loss rates), such as those described in International Publication No. WO/2007/124511, incorporated herein by reference. Porous, interconnected scaffolds can allow for and facilitate tissue (e.g., bone) cells to grow and proliferate such that the developing tissue(s) can replace the temporary scaffold material. For example, the scaffold material can have a controlled strength loss. In other embodiments, the mesoporous calcium composition can be a coating material.

In one embodiment, the mesoporous calcium silicate composition is biocompatible with bone or other tissue in the body of a human or other animal. For example, the compositions can be used alone or in combination with additional materials for dental implants, orthopedic implants, craniomaxillofacial applications, spinal grafting, etc. In other embodiments, the mesoporous calcium silicate compositions can be used alone, as a complement, and/or as an addition to other materials for forming bone implants and/or coatings for bone implants. In further embodiments, mesoporous calcium silicate compositions as disclosed herein can be packed into bone graft material (e.g., hydroxylapatite, bioactive glass, calcium phosphate ceramics, etc.), or used in bone pastes for providing a bioresorbable and biocompatible composition for regeneration or restoration of musculoskeletal tissue. In another embodiment, the mesoporous calcium silicate compositions can provide coatings for other types of bone grafts, such as an allograft or xenograft.

In some embodiments, the composition promotes bone in-growth and/or repair of damaged tissue. In vitro and in vivo studies have shown that calcium silicate ceramics could induce a bone-like apatite layer formation in simulated body fluid (SBF) [27] and chemically integrate into the structure of living bone tissue [28]. In one embodiment, the composition is used for regenerating tissue. The tissue can include at least one of bone, cartilage, muscle and musculoskeletal tissue. In many embodiments disclosed herein, the mesoporous calcium silicate is biocompatible as well as bioresorbable (e.g., allow the native tissues to gradually replace the implanted material). In one embodiment, the mesoporous calcium silicate is biocompatible with respect to at least one of eukaryotic cells, mammalian cells, bone forming cells, osteoblast cells, cartilage cells, muscle cells, stem cells, differentiated stem cells, bone marrow stem cells and nerve cells.

Some embodiments of mesoporous calcium silicate compositions further include at least one bioactive agent. Bioactive agents can include proteins, polypeptides, growth factors (e.g., human growth factors, osteoinductive growth factors), morphogens (e.g., bone morphogenic proteins), pharmaceutical drugs (e.g., a disease-specific drug, an osteoporotic drug, a symptom-treating drug, a pain relieving drug, etc.), chemicals, antibiotics, antimicrobial agents, vitamins (e.g., vitamin D, etc.), etc. The bioactive agent can be deposited on a surface, or in another embodiment, incorporated into the mesoporous calcium silicate compositions. In further embodiments, the bioactive agent can be stored within and/or on a surface of a scaffold material.

In many of the preceding embodiments, the bioactive agent can be incorporated or stored within the composition and/or scaffold material to provide for release and, more particularly, controlled release of the agent to facilitate restoration or regeneration of bone or other tissue. In some embodiments, the bioactive agent can be selectively released from the composition using one or more triggering mechanisms. For example, a triggering mechanism, such as application of electrical, magnetic, chemical or photochemical triggers can be used to selectively release the bioactive agent from the mesoporous calcium silicate composition at a time following implant. In some instances, the triggering event can include chemical ingestion, injection or infusion; exposure to UV light, ultrasound, magnetic fields, electric current, etc.

Wollastonite (e.g., calcium silicate) is a chain-silicate mineral which consists of a network of covalently bonded silica that is interrupted and modified by $Ca^{2+}$ cations [33, 34]. In one embodiment, synthesis of calcium silicate can include preparing a precipitation reaction of $Ca(NO_3)_2 \cdot 4H_2O$ and $Na_2SiO_3 \cdot 9H_2O$ at a 1:1 ratio.

Figure 1B:
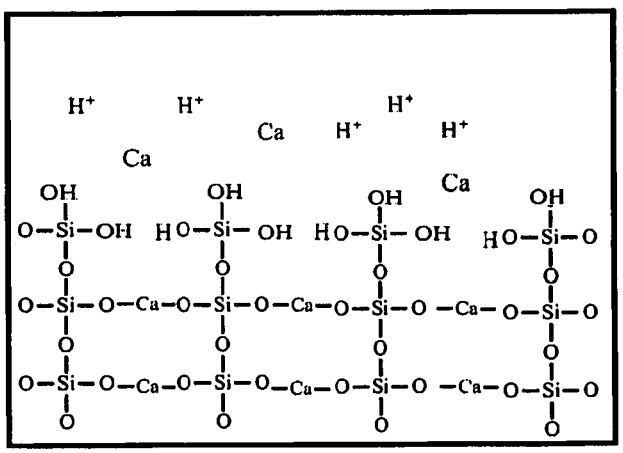
Figure 1C:
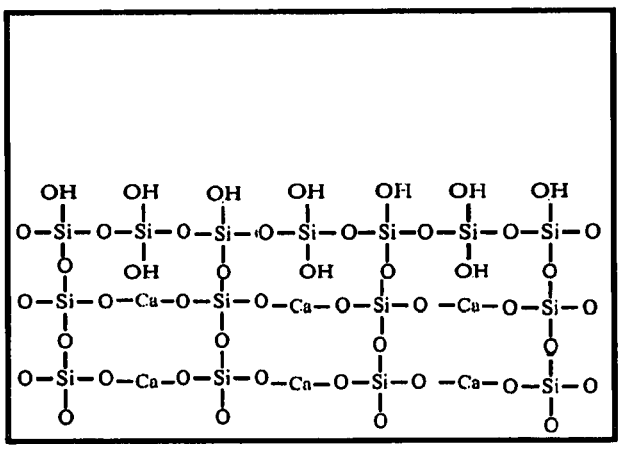

FIGS. 1A-1C illustrate a reaction mechanism of (A) wollastonite chain-silicate structure consisting of a network of covalently bonded silica that is interrupted and modified by Ca cations, (B) a reaction step wherein weakly bonded, network-modifying Ca is released relatively quickly to solution as Ca is exchanged for hydrogen ions and (C) a reaction step wherein silanol (Si—OH) in the leach layer repolymerizes to form a silica gel, and in accordance with an embodiment of the disclosure. Referring to FIGS. 1A and 1B, the weakly bonded, network-modifying $Ca^{2+}$ cations are released to solution (e.g., SBF) as they are exchanged for hydrogen ions, resulting in the formation of Si—OH, as shown below:

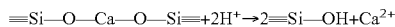

Silanol (Si—OH) can further repolymerize (FIG. 1C) to form silica gel by the following reaction:

In one embodiment, surface modification of wollastonite is applied by acid treatment, for example, to accelerate Si—OH formation on wollastonite particles and to form a mesoporous structure on the surface of wollastonite. Following acid modification, $Ca^{2+}$ is quickly leached from the wollastonite particles leaving only low or no Ca in an upper layer of the wollastonite particles. For example, calcium silicate formed from the precipitate reaction of $Ca(NO_3)_2 \cdot 4H_2O$ and $Na_2SiO_3 \cdot 9H_2O$, can be acid modified using a hydrochloric acid (HCl) solution. In some embodiments, HCL, or other acid, can be added to a slurry of calcium silicate until a neutral (e.g., 7.0) or acidic (less than 7.0) pH level is achieved. In further embodiments, HCL, or other acid, can be continuously added to maintain a selected pH (e.g., approximately pH 7.0, less than pH 7.0, less than pH 5.0, less than pH 1.0, approximately pH 0.5, etc.) for modification of the calcium silicate particles.

In some embodiments, acid modified calcium silicate particles have a mesoporous surface with nanoparticles. In some embodiments, the size of the nanoparticles is dependent on the conditions of the acid treatment (e.g., pH conditions, length of treatment, etc.). For example, in one embodiment, the size of the nanoparticles can be between 20 and 60 nm. In other embodiments, the size of the nanoparticles can be between 20 and 30 nm, between 40 and 60 nm, less than 75 nm, less than 30 nm, etc. The mesoporous surface of the acid-modified calcium silicate particles can have, in one embodiment, an average pore diameter of approximately 5 nm to approximately 4 nm. In other embodiments, the average pore diameter can be greater than 10 nm, less than 4 nm, between 10 nm and 4 nm, etc. The average pore diameter of the mesoporous structure can depend on the conditions of the acid treatment (e.g., pH conditions, length of treatment, etc.). Accordingly, one of ordinary skill in the art will recognize that the mesoporous calcium silicate particles can be formulated (e.g., using variable acid-modification conditions) such that the nanoparticle size and the average pore diameter are relatively selectable.

Acid modification of calcium silicate particles can also significantly increase a surface area of the particles (e.g., through formation of the mesoporous structure). Accordingly, mesoporous calcium silicate provides an increased surface area for adsorbing protein molecules and/or other bioactive materials. As such mesoporous calcium silicate shows higher protein adsorption, for example, than non-acid treated calcium silicate.

In some embodiments, it is desirable to have bioactive agents released continually over a certain or selectable period of time during a healing process or other tissue generation process. For unmodified calcium silicate, bioactive agents (e.g., protein) are adsorbed on the material surface by weak physical forces, e.g., Van Der Waals and electrostatic interaction [35]. Due to the nature of these bonding forces, the bioactive agents adsorbed by unmodified calcium silicate release quickly in the first several hours. In contrast, mesoporous calcium silicate compositions (e.g., acid-modified calcium silicate particles) have abundant O—H and Si—OH functional groups exposed on particle surfaces. Accordingly, bioactive agents (e.g., protein) can be bound to the mesoporous particle surface via hydrogen bonding with the Si—OH groups. Hydrogen bonding is stronger than the weak physical interactions observed on unmodified particles. Thus, the release kinetics of adsorbed bioactive agents from mesoporous calcium silicate compositions can be relatively slow and can be controllable.

In one embodiment, a release profile of the bioactive agent from a mesoporous calcium silicate composition includes a burst phase and an extended release phase. The burst phase can include an immediate release of a portion of the bioactive agent from the composition followed by the extended release phase. The extended release phase can include a slow release of the bioactive agent that extends for a plurality of days.

In another embodiment, the disclosure is directed to biocompatible compositions for controlled release of bioactive agents in bone replacement and/or tissue regeneration applications. The biocompatible composition can include mesoporous calcium silicate (CaSi) particles. In some embodiments, the mesoporous calcium silicate particles can have one or more bioactive agents adsorbed thereon or adsorbed therein. For example, the composition can include mesoporous CaSi particles with a combination of adsorbed bioactive agents, such as a combination of osteoinductive growth factor and vitamin D.

In a further embodiment, the composition can include a combination of mesoporous CaSi particles having different characteristics and/or bioactive agents. For example, a composition can include first and second portions of mesoporous CaSi particles. The first portion of mesoporous CaSi particles can have a first nanoparticle size, a first average pore diameter and a first bioactive agent adsorbed thereon for defining a first release kinetics profile of the first bioactive agent. The second portion of mesoporous CaSi particles can have a second nanoparticle size, a second average pore diameter and a second bioactive agent adsorbed thereon for defining a second release kinetics profile of the second bioactive agent. One of ordinary skill in the art will recognize that any number of combinations of mesoporous CaSi particles can be used to formulate a biocompatible composition having one or more desired bioactive agents, a desirable release kinetics profile, desired bioresorbable characteristics (e.g., degradation characteristics), etc.

In a further embodiment, a biocompatible composition for controlled release of bioactive agents in bone replacement and/or tissue regeneration applications can include various combinations of mesoporous CaSi particles and other resorbable ceramics, such as ceramics containing calcium phosphates (CaP) and calcium sulfates (CaS). In one embodiment, compositions including CaP and CaSi can be useful for providing compositions having selectable controlled release profiles for bioactive agents, selectable controlled strength loss rates within a select period of time, etc.

In some embodiments, a biocompatible composition for controlled release of bioactive agents in bone replacement and/or tissue regeneration applications can include a mesoporous calcium silicate-based material and/or a Ca-based ceramic (e.g., CaP, CaS) having at least one dopant included therein. In one embodiment, the dopant can include metal salts with metal ions; and in another embodiment, the dopant can include metal oxides. For example, the dopant can include one or more of $Zn^{2+}$, $Mg^{2+}$, $Si^{2+}$, $Na^+$, $K^+$, $Sr^{2+}$, $Cu^{2+}$, $Fe^{3+}/Fe^{2+}$, $Ag^+$, $Ti^{4+}$, $CO_3^{2-}$, $F^-$, MgO, ZnO, NaF, KF, $FeO/Fe_2O_3$, SrO, CuO, $SiO_2$, $TiO_2$, $Ag_2O$ and $CaCO_3$, present in a single-element or multi-element amount between 0 and about 10 wt %. In other embodiments, the dopant can be present in an amount from about 0.5 to about 5 wt %, from about 1 to about 3 wt %, from about 2 to about 5 wt. %, from about 3 to about 7 wt %, from about 4 to about 7 wt %.

In one embodiment, the dopant is present in an amount sufficient to maintain the compressive strength of the material (e.g., scaffold material, coating material, biocompatible composition, etc.) at about 30% of original or higher. In other embodiments, the dopant can be included in an amount sufficient to maintain the compressive strength of the material at about 40% of original or higher, 50% of original or higher, 60% of original or higher, etc. In other embodiments, the dopant is present in an amount sufficient to maintain the compressive strength of the material at about 70% to about 90% of original or higher. In a further embodiment, the dopant is present in an amount sufficient to lower the compressive strength of the material to about 90% of the original strength (e.g., without dopant) or less. In each of the above described embodiments, the material and/or composition can have a compressive strength maintained for a period of about 3 months to about 6 months under body, body fluid or simulated body fluid conditions, to provide for a fast-degrading composition. In other embodiments, the compressive strength can be maintained for a period of less than 3 months or greater than 6 months.

Accordingly, it can be appreciated that the mesoporous calcium silicate provides a drug delivery platform for controlled and/or sustained release of bioactive agents, such as protein and/or drugs, for therapy to a subject. For example, when placed in a subject as a graft, a coating, or other composition, the agent-loaded mesoporous calcium silicate can release the agent for an extended period of time, e.g., a period of days or weeks, providing a therapeutic amount of the bioactive agent to the subject, and at the target site (e.g., for tissue growth, bone replacement, bone regeneration, etc.).

In one embodiment, mesoporous calcium silicate compositions can be used as a vehicle for protein delivery with controlled release kinetics in vivo. Mesoporous calcium silicate can be synthesized from acid treatment (e.g., treatment with hydrochloric acid) of calcium silicate particles (e.g., powder). In one embodiment, mesoporosity of the surface of calcium silicate can provide increased surface area for protein (or other bioactive molecule) adsorption and retention as compared to unmodified calcium silicate. Acid treatment of calcium silicate also promotes the formation of Si—OH functional groups on the material surface, improving both biocompatibility of the particles as well as promoting strengthened bioactive agent interactions with the material surface.

B. EXAMPLES OF METHODS FOR SYNTHESIS AND CHARACTERIZATION OF MESOPOROUS CALCIUM SILICATE

The following examples are intended to demonstrate aspects of the disclosure more fully without acting as a limitation upon the scope of the disclosure, as numerous modifications and variations will be apparent to those skilled in the relevant art.

Example 1

Preparation of Calcium Silicate

To synthesize calcium silicate, CS powder was prepared from a precipitation reaction of $Ca(NO_3)_2.4H_2O$ and $Na_2SiO_3.9H_2O$ [31]. In this example, 1000 ml of 0.4 mol $Ca(NO_3)_2.4H_2O$ solution was stirred at room temperature, while 1000 ml of 0.4 mol $Na_2SiO_3.9H_2O$ was added dropwise over approximately 40-60 min to produce a white precipitate. The white precipitate was stirred for approximately 4 hours followed by washing five times with deionized water to remove excess $Na^+$ and $NO_3^-$ ions. The precipitate was then washed two times with 100% ethanol to improve dispersion characteristics. The obtained powder was dried at approximately 80° C. for about 24 hours.

Example 2

Preparation of Mesoporous Calcium Silicate

A mesoporous structure of calcium silicate can be produced by acid treatment of the CS powder prepared as in Example 1 using a hydrochloric acid (HCl) solution. In this example, CS powder was dispersed in deionized water to produce a slurry with a powder/water weight ratio of 1:10. The pH of the starting slurry was about 11. Next, the slurry was separated into four samples, in which 1N HCl solution was added dropwise to adjust the pH of three samples, while a final sample was not pH adjusted. The three pH-adjusted CS powder samples were individually adjusted to a pH of 7.0, a pH of 4.5, and a pH 0.5. The pH of the slurry increases gradually due to the reaction between calcium silicate and HCl. Accordingly, HCl solution was added continuously to keep the pH of the slurry constant. Following acid treatment for 40 min at their respective pH values, the powders were washed with deionized water and dried at 100° C. over night. The powders discussed herein and prepared according to this exemplary process at an exemplary slurry pH of 7.0, 4.5, and 0.5 are referred to as CS-7.0, CS-4.5, and CS-0.5, respectively. Non-acid treated calcium silicate slurry is referred to as CS.

The following example describes methods for characterization of calcium silicate before and after acid treatment (e.g., as prepared in Examples 1 and 2 described above) and results of such characterization are shown in FIGS. 2-6C.

Example 3

Characterization of Mesoporous Calcium Silicate

The morphologies of acid-treated calcium silicate particles were observed using a scanning electron microscope (FESEM; FEI, SIRION, OR). The chemical compositions of calcium silicate particles before and after acid modification were examined by energy-dispersive X-ray spectroscopy (EDS). An X-ray diffractometer (XRD; PW 3040/00 X'pert MPD, Philips, Eindhoven, the Netherlands) was used to analyze the phase composition of calcium silicate particles. Infrared spectra were recorded by a Fourier transform infrared spectrometer (FTIR, Nicolet 6700, ThermoFisher, Madison, Wis.). Composition structure analysis of calcium silicate before and after acid modification was demonstrated by a $^{29}Si$ magic-angle spinning (MAS) nuclear magnetic resonance (NMR) study. MAS NMR was performed on a Varian Inova 500 (11.75 T) spectrometer operating with a magnetic filed of 79.5 MHz and a spinning rate of 4 kHz. A 7 mm zirconia rotor was used for all experiments. Cross-polarization (from proton) spectra were collected for 10,000 scans with a recycle interval of 6 seconds. Chemical shifts are referenced using an external standard of tetramethylsilane (TMS).

Figure 2:
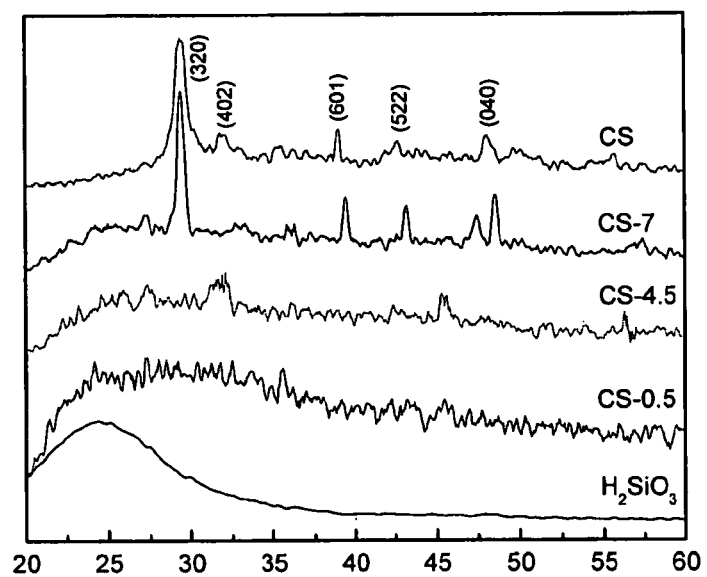

FIG. 2 is a XRD spectra of calcium silicate before (CS) and after acid modification (CS-7, CS-4.5, CS-0.5) in accordance with an embodiment of the disclosure. As shown in FIG. 2, samples having acid modification show an amorphous hump between the 20° and 30° regions, which can be attributed to the presence of hydrated silica. This hump was more obvious when calcium silicate was treated at a lower pH value (e.g., pH of 0.5). Referring to FIG. 2, the spectrum of CS-0.5 was similar to that of silicic acid ($H_2SiO_3$).

Table 1 shows the results of EDS analysis of calcium silicate (CS) before and after acid modification. As shown in the second column, Ca content decreased significantly following acid modification.

TABLE 1

EDS analysis of Calcium Silicate before and after acid modification.

| Material | Ca (at %) | Si (at %) | O (at %) |
|---|---|---|---|
| CS | 18.83 | 23.05 | 58.12 |
| CS-7 | 7.36 | 27.20 | 65.44 |
| CS-4.5 | 1.37 | 28.81 | 69.83 |
| CS-0.5 | — | 28.44 | 71.56 |

The leaching of $Ca^{2+}$ from CS results in the formation of a modified surface layer which is calcium depleted and silicon enriched. When modified at a lower pH, more calcium silicate can react with HCl. For example, when treated at pH 0.5, mesoporous CS transformed completely into hydrated silica, and no calcium was detected by EDS, as shown in table 1.

Figure 3:
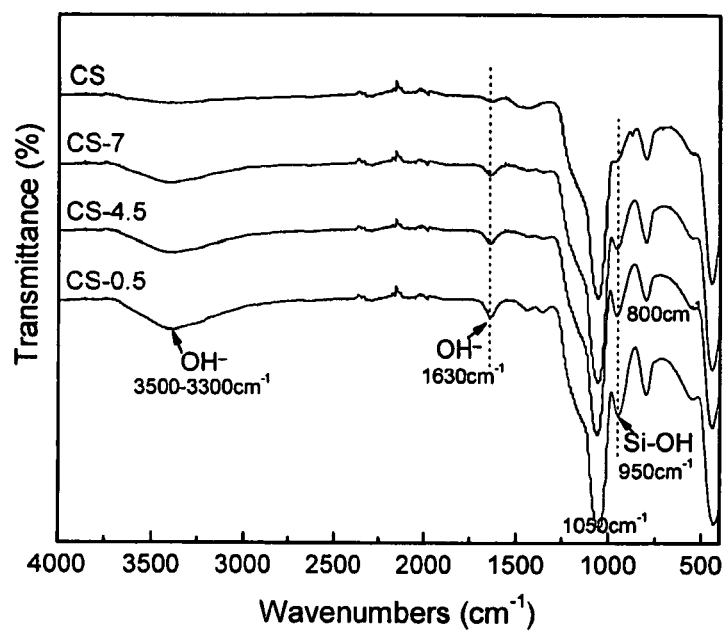

FIG. 3 is a FTIR spectra of calcium silicate before and after acid modification in accordance with an embodiment of the disclosure. As shown in FIG. 3, CS showed strong adsorption at 1050 and 800 $cm^{-1}$, which can be attributed to the Si—O—Si stretching vibration. The band near 450 $cm^{-1}$ corresponds to the Si—O bond rocking [36]. The significant difference between the particles before and after modification appeared at 950 $cm^{-1}$ and can be interpreted as Si—OH bond stretching. The band at 1630 $cm^{-1}$, which arose from the O—H bending, was also found after modification. The bump in the 3500-3300 $cm^{-1}$ regions, due to O—H stretching and adsorbed water, was apparent in the acid-modified particle spectra [36]. As demonstrated and shown in FIG. 3, bands representing Si—OH and O—H increase with a decrease of pH value.

Figure 4:
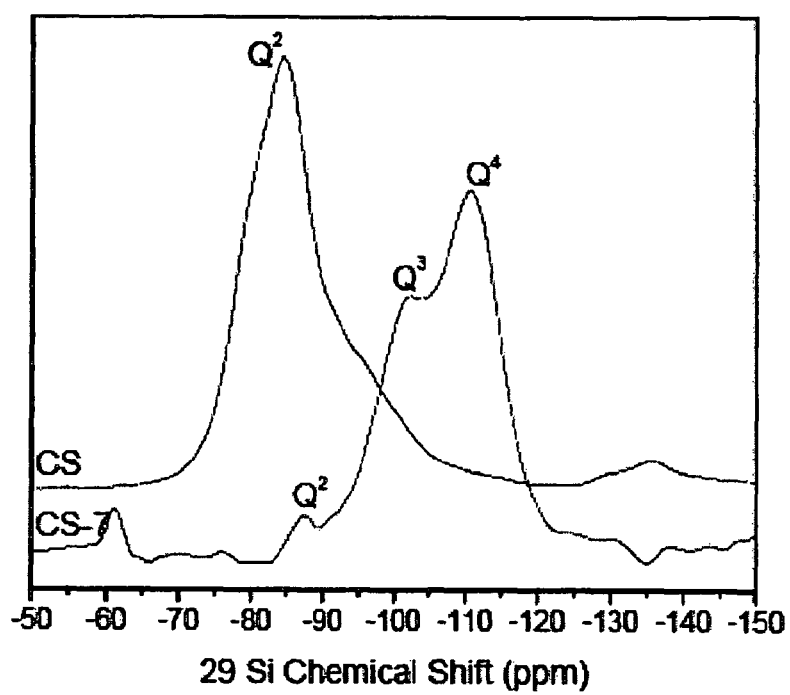

The chemical shift of $^{29}Si$ is affected by the silicon coordination number and by its first neighbors (bridging and nonbridging oxygen). The $Q^n$ species (where n=0-4 is the number of bridging oxygen molecules) all exhibit different chemical shifts, and can thus theoretically be separated by NMR [42]. FIG. 4 is a $^{29}Si$ magic-angle spinning (MAS) nuclear magnetic resonance (NMR) analysis of calcium silicate before (CS) and after (CS-7) acid modification in accordance with an embodiment of the disclosure. Referring to the MAS NMR results shown in FIG. 4, non-acid modified calcium silicate (CS) demonstrates a major peak $Q^2$ near −85 ppm. The major peak $Q^2$ has previously been demonstrated for silicate chains [37]. Following acid modification at pH 7.0, the $Q^2$ peak is minimally detectable, while hydroxylated (OH) $Q^3$ (at −102 ppm) and $Q^4$ (at −110 ppm) peaks are observed. Peaks $Q^3$ and $Q^4$ have previously been demonstrated for silica gel [37]. The results indicate the formation of silica gel reactive layer with OH group after acid modification, which is consistent with the results from the XRD and FTIR analyses.

Figure 5A:
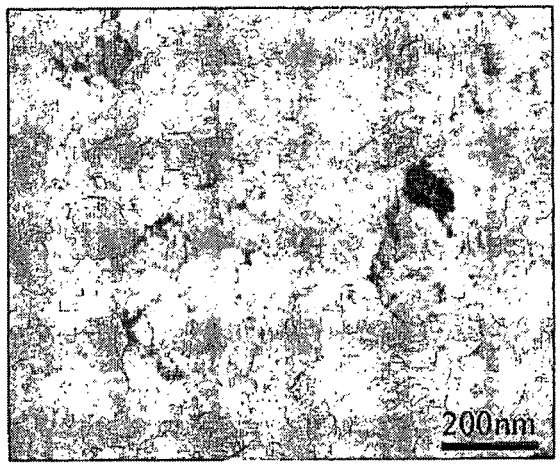
Figure 5B:
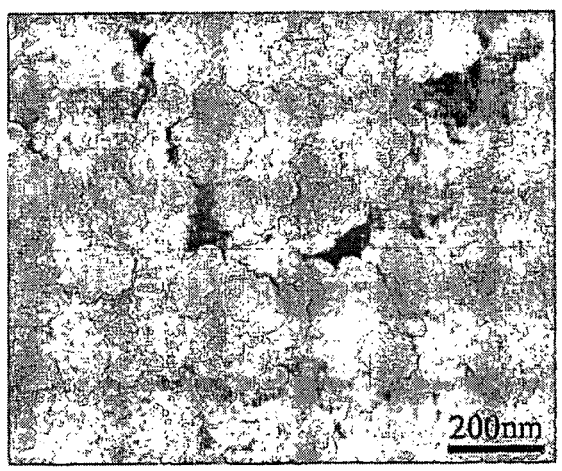
Figure 5C:
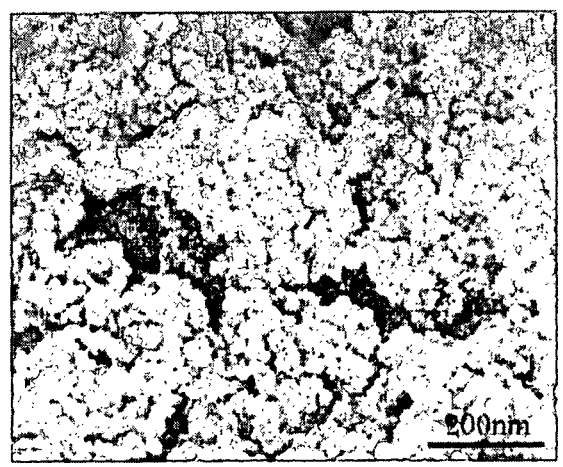

FIGS. 5A-5C are, respectively, scanning electron microscopy (SEM) images of morphologies and microstructures of calcium silicate following acid treatment at (A) pH 7.0, (B) pH 4.5 and (C) pH 0.5, and in accordance with an embodiment of the disclosure. The reactive layer on the surface of calcium silicate following acid modification showed porous nanostructures. The size of these newly formed nanoparticles on sample CS-7 was between 40 and 60 nm. Following treatment at pH 0.5, the nanoparticle size was further decreased to between 20 and 30 nm.

To calculate pore size, the CS powder samples were characterized by nitrogen gas adsorption/desorption isotherms at 77 K and measured using a surface analyzer (TRISTAR 3000, Micromeritics, Norcross, Ga.). In this example, samples were pretreated by heating at approximately 300° C. for 4 hours to remove physically adsorbed gases and/or moisture from the sample surfaces. Pore size distributions were calculated from the desorption branch of the isotherm using the Barrett-Joyner-Halenda (BJH) method, and surface areas were measured using the Brunauer-Emmett-Teller (BET) method.

Figure 6A:
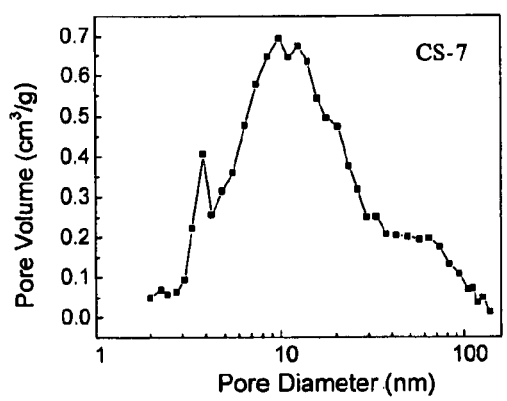
Figure 6B:
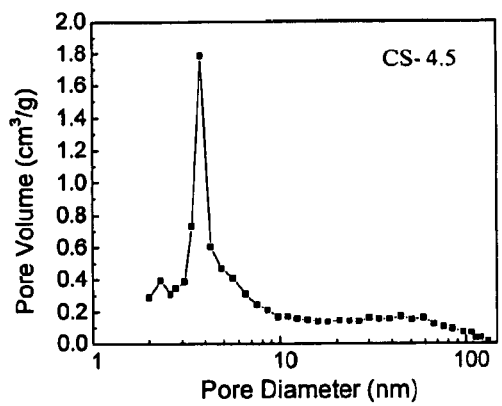
Figure 6C:
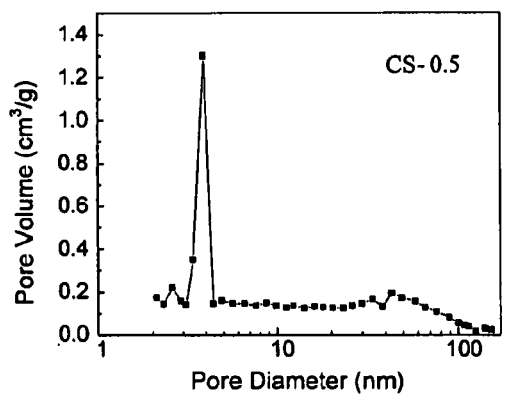

FIGS. 6A-6C are, respectively, graphical representation of a pore size distribution for mesoporous calcium silicate samples CS-7, CS-4.5 and CS-0.5, and in accordance with an embodiment of the disclosure. FIG. 6A shows CS-7 having a wide pore size distribution; however, a sharp peak detected at around 4 nm suggests a mesoporous reactive layer formation at the particle surface. FIGS. 6B and 6C show CS-4.5 and CS-0.5, respectively, having a narrow pore size distribution when compared to the pore size distribution observed for CS-7 samples. For example, the average pore diameter was 5.0 nm for CS-4.5 and 4.4 nm for CS-0.5.

Table 2 shows the BET specific average surface areas for mesoporous calcium silicate samples before and following acid modification.

TABLE 2

Properties of Mesoporous Calcium Silicate

| Material | BET surface area ($m^2/g$) | Pore volume ($cm^3/g$) | Average pore diameter (nm) |
|---|---|---|---|
| CS | 65.5 | | |
| CS-7 | 221.3 | 0.575 | 9.7 |
| CS-4.5 | 332.9 | 0.475 | 5.0 |
| CS-0.5 | 356.2 | 0.582 | 4.4 |

The BET surface area of non-acid modified CS was 65.5 m²/g. In contrast, mesoporous calcium silicate samples having acid modification demonstrate an increase in BET surface area. For example, following acid treatment of calcium silicate at pH 7, 4.5 or 0.5, BET surface areas were 221.3 m²/g, 332.9 m²/g and 356.2 m²/g, respectively.

XRD analysis of acid modified calcium silicate under different conditions showed the formation of an amorphous silicon-enriched layer, which was similar to silicic acid (FIG. 2). In FIG. 3, FTIR further demonstrated this reactive layer contained high amounts of O—H and Si—OH (silanols) groups. These results indicate that a hydrated silica gel layer having abundant Si—OH bioactive groups was formed on the surface of calcium silicate following acid modification.

Furthermore, acid modification creates a mesoporous surface layer on calcium silicate. FESEM microstructure analysis showed that following acid modification, the newly formed silica gel reactive layer has nanostructures, with particle sizes between 20 and 30 nm after treatment at pH 0.5 (FIG. 5C). Nitrogen gas adsorption studies showed the size of these pores was about 4-5 nm. These mesoporous structures increase the surface area on the calcium silicate particles, which can absorb higher levels of protein and other bioactive agents.

Example 4

Protein Adsorption by Mesoporous Calcium Silicate

Protein adsorption by mesoporous calcium silicate samples was quantified. In this example, estimation of the amount of protein adsorbed by mesoporous calcium silicate was determined using bovine serum albumin (BSA, A7030, Sigma, Saint Louis, Mo.) and lysozyme from chicken egg white (L6876, Sigma, Saint Louis, Mo.) as model proteins. Some of the physical properties of BSA and lysozyme are listed in Table 3 [35].

TABLE 3

Physical Properties of Model Proteins

| Protein | Molecular mass (Da) | Isoelectric point | Dimension (nm) |
| --- | --- | --- | --- |
| BSA | 66,400 | 4.7 | 4 × 4 × 14 |
| Lysozyme | 14,400 | 11 | 3 × 3 × 4.5 |

In this example, 50 mg of non-acid modified and acid modified calcium silicate particles (e.g., powder), prepared according to Example 2 above, were immersed in 20 milliliters of a 1 mg/ml solution of either BSA or lysozyme at 37° C. The methods described herein were carried out at selected pH values with phosphate buffer solution (pH=7.0) and acetic buffer solution (pH=4.5). At selected time points, the slurries were centrifuged and the amounts of proteins in the supernatants were measured by Micro BCA™ protein assay kit (Pierce, Rockford, Ill.). The protein amount loaded on CS and mesoporous calcium silicate was calculated by determining the change in protein concentration in solution. Precipitates in the centrifuged solution were filtered, washed with distilled water and dried for approximately 48 hours at room temperature in open air. Changes in pore structure and surface chemistry of the particles following protein adsorption were determined through nitrogen adsorption and FTIR, using the methods described above.

Figure 7B:
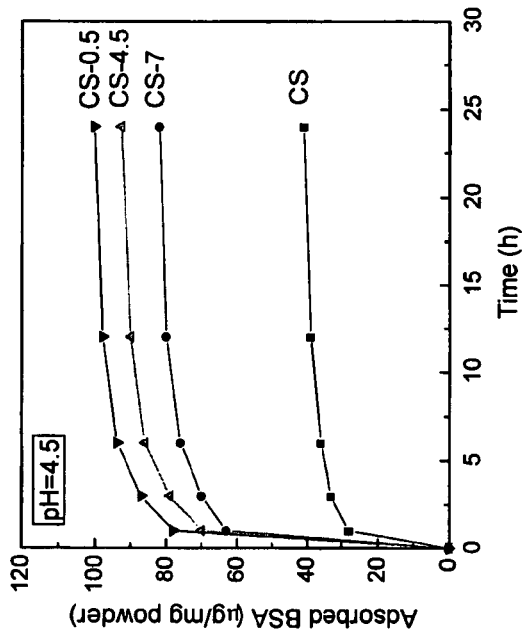
Figure 7A:
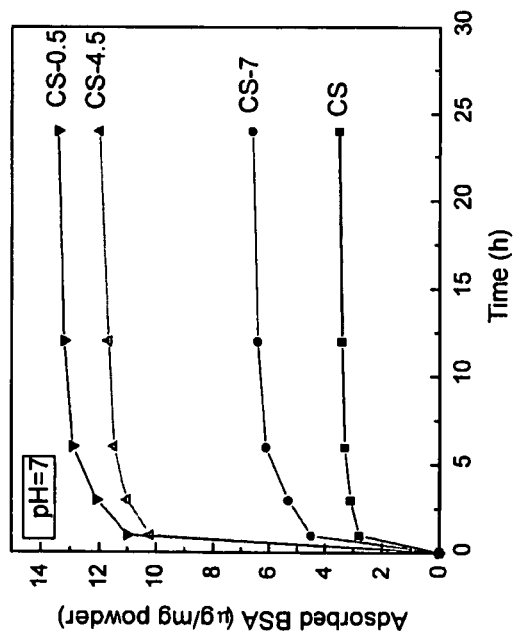

FIGS. 7A-7B are graphical representations of the kinetics of BSA adsorption by non-acid modified calcium silicate (CS) and by mesoporous calcium silicate (mesoporous CS) in accordance with an embodiment of the disclosure. FIG. 7A shows that CS and mesoporous CS samples immersed in a solution maintained at a pH of 7.0 exhibit low BSA adsorption. In contrast, FIG. 7B shows that mesoporous CS samples immersed in a solution maintained at a pH of 4.5 exhibit an increase in BSA adsorption compared to samples immersed at pH 7.0 and to CS samples. As shown in FIGS. 7A and 7B, the equilibrium capacity for BSA adsorption at pH 4.5 by CS-0.5, CS-4.5 and CS-7 particles was 100, 93 and 82 µg/mg, respectively.

Figure 8:
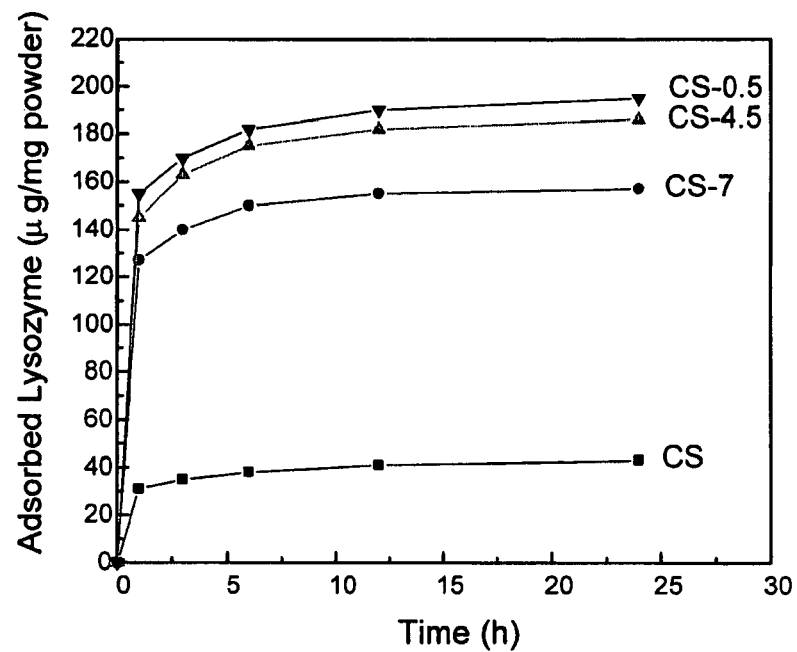

FIG. 8 is a graphical representation of the kinetics of lysozyme adsorption by non-acid modified calcium silicate (CS) and by mesoporous calcium silicate (mesoporous CS) at a pH of 7.0 in accordance with an embodiment of the disclosure. In comparison to the kinetics of BSA absorption at pH 7.0 shown in FIG. 7A, the adsorption kinetics of lysozyme by calcium silicate is higher and adsorption by mesoporous CS is significantly higher. As shown in FIG. 8, the equilibrium capacity was 195, 186 and 157 µg/mg of wollastonite for CS-0.5, CS-4.5 and CS-7, respectively. As shown in FIG. 8, the equilibrium capacity for lysozyme adsorption by CS-0.5, CS-4.5 and CS-7 all demonstrate significantly higher loading than the 43 µg/mg equilibrium capacity for CS.

In this example, mesoporous CS demonstrated significantly higher protein loading (e.g., higher levels of protein adsorption) than unmodified CS. The higher protein loading capacity observed for mesoporous CS can be attributed to the formation of Si—OH functional groups in the mesoporous surface layer.

Figure 9:
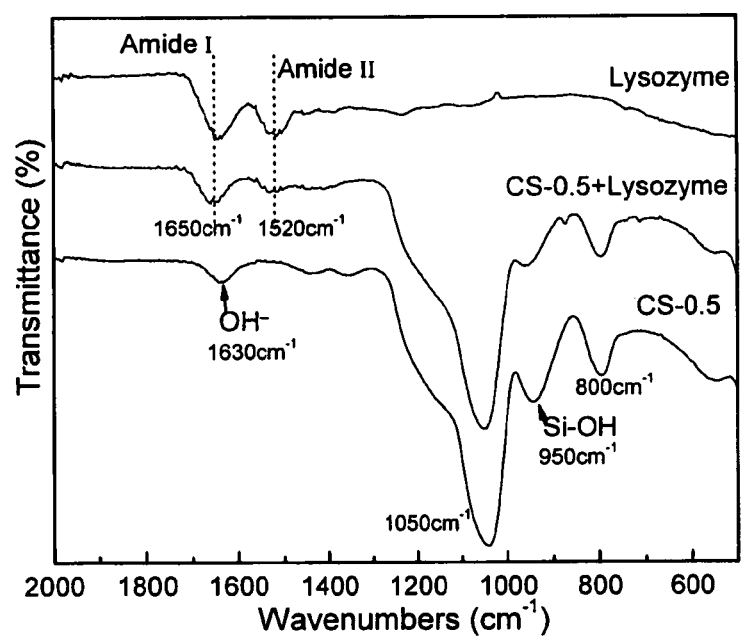

Changes in surface chemistry of mesoporous CS particles following absorption of lysozyme were analyzed by FTIR. FIG. 9 shows the FTIR spectra of mesoporous calcium silicate before and following lysozyme adsorption in accordance with an embodiment of the disclosure. The amide I band near 1650 cm$^{-1}$ is attributed to the C=O stretching mode, and the amide II band near 1520 cm$^{-1}$ is attributed to the bending and the stretching mode of N—H and C—N vibrations [35]. Following lysozyme protein loading on the mesoporous calcium silicate samples, the amide I and amide II bands can be clearly identified. Additionally, FIG. 9 shows that the OH$^-$ band at 1630 cm$^{-1}$ and Si—OH band at 950 cm$^{-1}$ (seen in the FTIR spectra of CS-0.5 without lysozyme) decreased significantly following lysozyme protein adsorption (seen in the FTIR spectra of CS-0.5+lysozyme), indicating interactions between protein molecules and Si—OH groups.

Retaining structural conformation and bioactivity of loaded proteins can be important for protein delivery. Amide I and amide II bands are typically used for indication of lysozyme structure integrity. The amide I band is due to the α-helical conformation of lysozyme, and the amide II band can be attributed to the parallel β-sheet structure of lysozyme [35]. Therefore, the appearance of amide I and amide II bands indicates that the structural conformation of lysozyme is retained and does not denature after adsorption on mesoporous calcium silicate.

Figure 10:
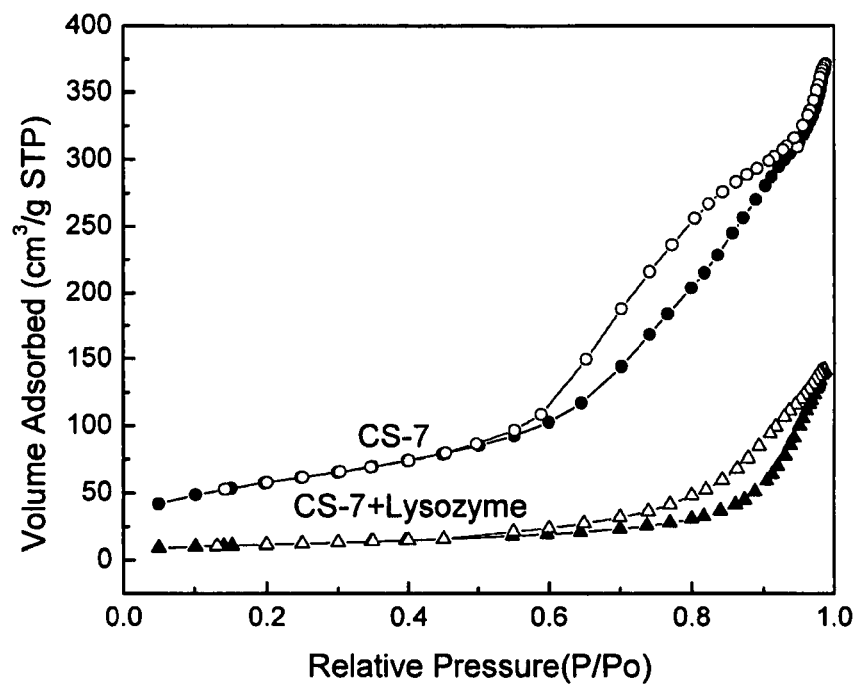

Changes in pore structure of mesoporous CS particles following absorption of lysozyme were determined by nitrogen absorption. FIG. 10 is a graphical representation of nitrogen adsorption isotherms of CS-7 before and following lysozyme adsorption in accordance with an embodiment of the disclosure. As shown in FIG. 10, the amount of nitrogen absorbed by the mesoporous CS particles decreased following lysozyme adsorption. Surface area of mesoporous calcium silicate following lysozyme adsorption was calculated using the BET method as described above. The BET specific average surface areas and pore volumes of mesoporous CS samples CS-7, CS-4.5 and CS-0.5 are shown in Table 4.

TABLE 4

Properties of Mesoporous Calcium Silicate following Lysozyme Adsorption

|                  | BET surface area ($m^2/g$) | Pore volume ($cm^3/g$) | Average pore diameter (nm) |
|------------------|----------------------------|------------------------|----------------------------|
| CS-7 + lysozyme   | 90.5                       | 0.26                   | 9.2                        |
| CS-4.5 + lysozyme | 142.6                      | 0.3                    | 4.4                        |
| CS-0.5 + lysozyme | 139.4                      | 0.39                   | 4.1                        |

Comparing the results in Tables 1 and 4, both the BET specific average surface areas as well as the pore volumes of all mesoporous CS samples were reduced following lysozyme adsorption.

Comparison of FIGS. 7A and 8 show that mesoporous calcium silicate has a higher adsorption capacity for lysozyme that BSA. The dimension of BSA, which is about 4×4×14 nm3, is much larger than lysozyme, which has dimensions measuring 3×3×4.5 nm3 [35]. Accordingly, lysozyme may demonstrate more efficient loading into the nanoscale pores of the mesoporous CS particles than BSA due to its smaller size. For example, the large reduction in the BET specific average surface area and pore volume (Table 4) can be attributed to the tight packing of lysozyme molecules into the pores of mesoporous CS. These results suggest that for mesoporous structures, the size of a protein molecule (or other bioactive molecule) may affect the efficiency of its adsorption.

Electrostatic interactions between protein molecules (or other bioactive molecules) and adsorbent materials can be a factor for efficient loading/adsorption. At pH 7.0, mesoporous CS particles are negatively charged. BSA, which has an isoelectric point of 4.7, is also negatively charged at a pH 7.0. Therefore, the repulsive interaction between BSA protein molecules and mesoporous CS particles restricts the amount of BSA adsorbed. In contrast, the surface charge of BSA has a negligible repulsive interaction with mesoporous CS particles treated at pH 4.5 which can result in the remarkable increase of BSA adsorption capacity (FIG. 6).

In addition to electrostatic interaction, the Si—OH groups formed on the surface of wollastonite particles also play a role in protein adsorption. Protein molecules contain hydroxyl groups and amino groups, which can form hydrogen bonding with Si—OH. FTIR analysis (shown in FIG. 3), showed a decrease in the Si—OH (950 $cm^{-1}$) band after protein adsorption, suggesting an interaction between the protein molecules and the Si—OH groups. Due to the presence of abundant O—H and Si—OH groups in acid modified particles, acid modified wollastonite displays higher protein adsorption capacity than unmodified wollastonite.

Mesoporous structure with high surface area is also suggested to be beneficial to protein adsorption [35]. The porous structure resulting from acid modification has small pore sizes (e.g., about 4-5 nm). These small pores are not accessible for BSA adsorption due to the larger dimensions of BSA, which is about 4×4×14 $nm^3$. Lysozyme, which is a smaller protein with dimensions of 3×3×4.5 $nm^3$, can be absorbed into the mesopores of wollastonite. This can be a reason for higher adsorption capacity achieved for lysozyme compared to BSA. Lysozyme adsorption into the mesopores can be confirmed by nitrogen adsorption isotherms of mesoporous wollastonite before and after protein loading. The large reduction in the special surface area and pore volume can be attributed to the tight packing of lysozyme molecules in the pores of mesoporous wollastonite.

Example 5

Protein Release from Mesoporous Calcium Silicate

In this example, lysozyme protein-loaded (e.g., approximately 50 mg) mesoporous calcium silicate particles were prepared as described in Example 4 above, and the samples were immersed in about 20 milliliters of acetic buffer solution (pH=4.5) or in about 20 milliliters of phosphate buffer solution (pH=7.0). At selected time points, slurries were centrifuged and released protein in the supernatant was measured by Micro BCA™ protein assay kit.

Figure 11A:
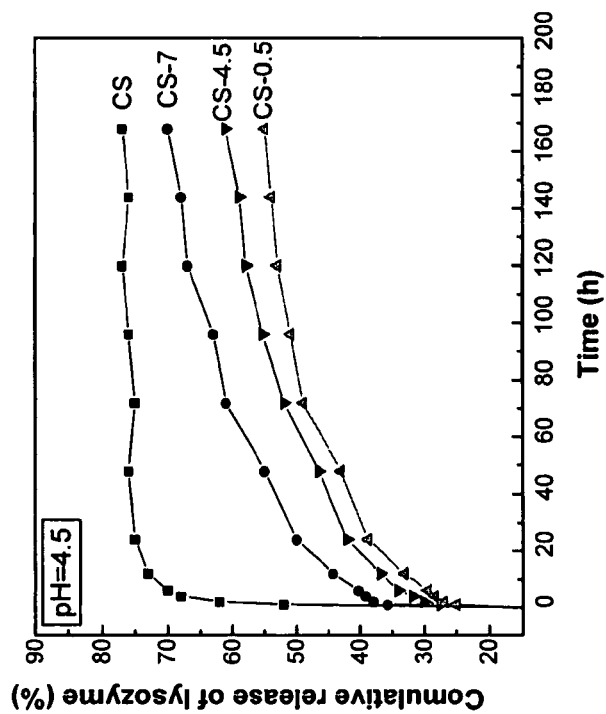
FIGS. 11A-11B are, respectively, graphical representations of cumulative release kinetics of lysozyme from calcium silicate at (A) pH 7 and (B) pH 4.5 in accordance with an embodiment of the disclosure.
Figure 11B:
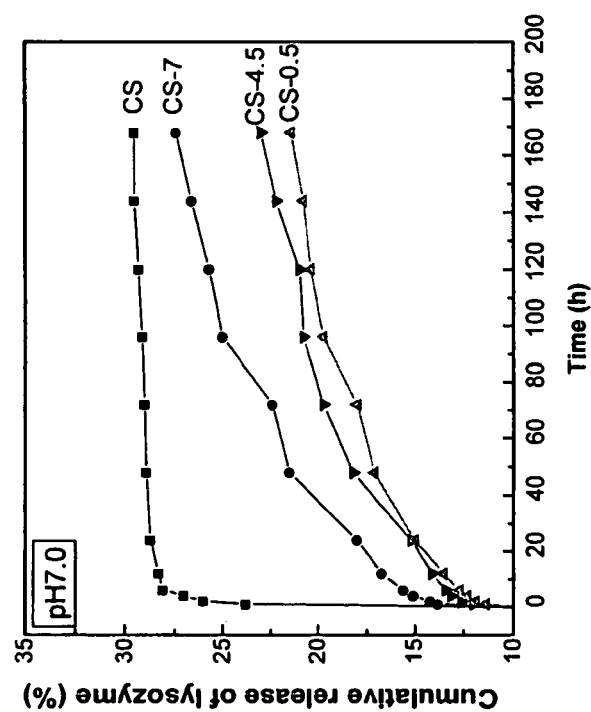

FIGS. 11A-11B are graphical representations showing the cumulative release kinetics of lysozyme from protein-loaded calcium silicate and mesoporous calcium silicate samples in accordance with an embodiment of the disclosure. As shown in FIG. 11A, the release rate of lysozyme protein from CS at a solution pH of 7.0 was very rapid. For example, an initial burst of released protein (e.g., about 28%) was detected in the supernatant within the first 6 hours. The protein concentration of the supernatant remained nearly constant over the next 7 days, indicating no further or little release of protein from the CS particles following the initial burst. In contrast to the release kinetics demonstrated by lysozyme protein loaded CS, FIG. 11A shows differing protein release kinetics for the lysozyme protein loaded mesoporous CS particles. As shown, the release kinetics displayed a two-step release pattern including an initial small burst release followed by a relatively slow sustained release over the following 7 days. The initial burst in the first 6 hours for CS-7, CS-4.5 and CS-0.5 samples was around 16.7%, 14.1% and 13.5%, respectively. Although the rate at which the protein was released decreased during the next 7 days, gradual protein release from the mesoporous CS samples was still detectable. After 7 days, the cumulative amount of released protein for CS-7, CS-4.5 and CS-0.5 was 26.8%, 22.2% and 20.8%, respectively.

FIG. 11B shows the release rate of lysozyme protein from CS and mesoporous CS samples. As shown, the release rates of all samples at a solution pH of 4.5 demonstrated a remarkable increase over the release rates of the same samples at a solution pH of 7.0 (FIG. 11A). At pH 4.5, the cumulative 7 day lysozyme protein release for CS-7, CS-4.5 and CS-0.5 was 68%, 59% and 54%, respectively.

Example 6

Degradation of Mesoporous Calcium Silicate

In this example, estimation of the degradation rate of mesoporous calcium silicate of Example 2, was determined. 50 mg of mesoporous CS particles was immersed in 20 ml of acetic buffer solution (pH=4.5) or in 20 ml phosphate buffer solution (pH=7.0). At selected time points, mesoporous CS particles were centrifuged and dried at 100° C. overnight. The degradation rate was calculated by weight change of the mesoporous CS particles before and following immersion.

Figure 12:
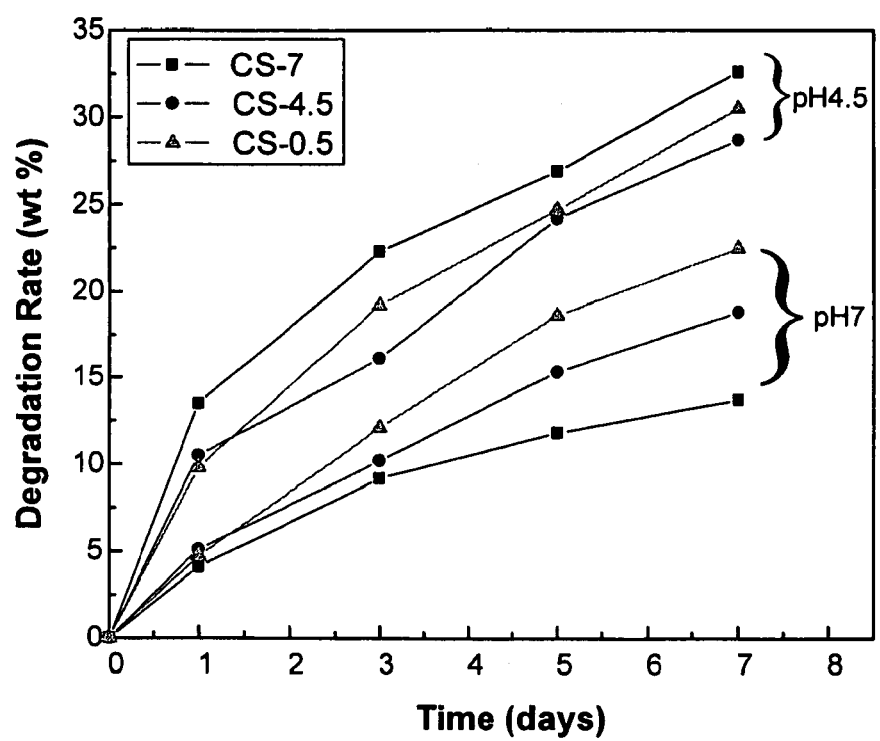
FIG. 12 is a graphical representation of a degradation rate of mesoporous calcium silicate at pH 7 and pH 4.5 in accordance with an embodiment of the disclosure.

FIG. 12 is a graphical representation of the degradation rate of mesoporous calcium silicate in accordance with an embodiment of the disclosure. As shown, mesoporous calcium silicate exhibits a high degradation rate over 7 days. For samples immersed in phosphate buffer solution at a pH of 7.0, the amount of degraded mesoporous CS at day 7 for CS-7, CS-4.5 and CS-0.5 was around 13.7%, 18.8% and 22.5%, respectively. Additionally, the degradation rate of mesoporous CS samples immersed in acetic buffer solution at a pH of 4.5 was remarkably increased compared to samples incubated at a pH of 7.0.

As described above in Example 5, mesoporous calcium silicate particles display a two-step release pattern including a small initial burst release followed by a relatively slow sustained release, (FIGS. 11A-11B). The initial burst release can be attributed the release of protein molecules adsorbed on an exterior surface of the mesoporous CS particles. The entrapped proteins in the mesoporous structures can be released slowly as the support structure (the mesoporous CS material) degrades. Accordingly, the mesoporous structures can provide sustained release kinetics over a longer period of time. Calcium silicate shows higher degradation rates when immersed in solutions at pH 4.5 as compared to solutions at pH 7.0 (FIG. 12). These degradation rates support faster release of protein at a lower pH when compared to a high pH.

Example 7

Biocompatibility of Mesoporous Calcium Silicate

Calcium silicate (CS) has been regarded as a candidate for bone replacement biomaterial due to its good bioactivity properties. In vitro and in vivo studies showed that CS ceramic could induce a bone-like apatite layer formation in simulated body fluid (SBF) [27] and chemically integrate into the structure of living bone tissue [28]. To improve the mechanical properties, CS coating on titanium alloy was also developed by plasma spray [29, 30]. Additionally, nano-sized calcium silicate particles were synthesized and its biocompatibility was demonstrated by an in vitro study [31, 32]. The analyses of these in vitro and in vivo studies reveal that the primary reason for biocompatibility of calcium silicate is the formation of Si—OH on its surface when exposed to body fluid.

In this example, biocompatibility of calcium silicate and mesoporous calcium silicate particles (e.g., powder) with human fetal osteoblast cells was evaluated in vitro. CS and mesoporous CS samples (e.g., CS-7, CS-4.5, CS-0.5) were sterilized by autoclaving at 121° C. for 30 minutes. An established human fetal osteoblast cell line, hFOB 1.19 (ATCC, Manassas, Va.), was used in this study. The cells were seeded in 24-well plates with 5 g of calcium silicate (CS or mesoporous CS) particles per well. Initial cell density was about $2.0 \times 10^4$ cells per well. The base medium used for this cell line was a 1:1 mixture of Ham's F12 Medium and Dulbecco's Modified Eagle's Medium (DMEM/F12, Sigma, St. Louis, Mo.), having 2.5 mM L-glutamine (without phenol red). The medium was supplemented with 10% fetal bovine serum (HyClone, Logan, Utah) and 0.3 mg/ml G418 (Sigma, St. Louis, Mo.). Cultures were maintained at 34° C. under an atmosphere of 5% $CO_2$. Medium was changed every 2-3 days for the duration of the experiment.

Cell proliferation was evaluated using an MTT (3-(4,5-dimethylthiazol-2-yl)-2,5-diphenyl tetrazolium bromide) assay following 1, 4 and 7 days of incubation. An MTT (Sigma, St. Louis, Mo.) solution of 5 mg/ml was prepared by dissolving MTT in PBS, followed by filter sterilization using a 0.2 micron pore filter paper. The MTT solution was diluted 1:9 (50 µl into 450 µl) in DMEM/F12 medium, and 500 µl of diluted MTT solution was then added to each sample in the 24-well plates. After 2 hours of incubation, 500 µl of solubilization solution made up of 10% Triton X-100, 0.1N HCl and isopropanol were added to the wells to dissolve the formazan crystals. 100 µl of each resulting supernatant was transferred into a 96-well plate, and read by a plate reader at 570 nm. Data are presented as mean±standard deviation. Statistical analysis was performed using Student's t-test, and $P<0.05$ was considered statistically significant. CS samples were used as controls for evaluating cell proliferation of hFOB cells incubated with mesoporous CS samples.

FIG. 13 is a graphical representation of cell densities of human fetal osteoblast cells cultured with samples of CS and mesoporous CS in accordance with an embodiment of the disclosure. As shown, cell proliferation was evident for hFOB cells in culture with CS and mesoporous CS samples following 1, 4 and 7 days. As shown in FIG. 13, for each CS or mesoporous CS sample, cell density increased with an increase in culture time. Statistical analysis showed that cell density on mesoporous CS samples was significantly higher than those on unmodified CS samples.

To observe cell-material interaction, calcium silicate and mesoporous calcium silicate powders were pressed by uniaxial pressing with a pressure of 10 MPa, and sintered at 1100° C. for 2 hours. Human fetal osteoblast cells (hFOB cells) were seeded onto the pressed samples with the in vitro seeding process as described above. After culturing for 3 and 7 days, samples were fixed with 2% paraformaldehyde/2% osmium tetroxide ($OsO_4$) for 2 hours at room temperature. The fixed samples were then dehydrated in an ethanol series (30%, 50%, 70% 95% and 100% three times), followed by a hexamethyldisilane (HMDS) drying procedure. After gold coating, the samples were observed under SEM for cell morphologies.

FIGS. 14A-14B are SEM images of morphologies of cells cultured on pressed mesoporous calcium silicate (CS-7) after 3 days (14A) and 7 days (14B) of culture in accordance with an embodiment of the disclosure. As shown in FIG. 14A, cells exhibited a typical osteoblast phenotype with some lamellipodia and filopodia extensions, indicating good cell attachment and spreading on the mesoporous CS-7 surface. After 7 days of culture, a confluent layer of cells were observed on the CS-7 material surface (FIG. 14B).

The osteoblast cell culture test shows that CS has good biocompatibility, and hFOB cells attach and proliferate on CS. Compared to unmodified CS particles, mesoporous CS powders display higher biocompatibility. Unmodified CS may undergo a reaction in cell culture medium resulting in a decrease in pH of the media. This pH decrease may attenuate cell growth. The mesoporous CS samples have been shown to be stable in the cell culture medium. Another important reason for high biocompatibility of mesoporous CS may be attributed to the active OH groups on the acid-modified CS surface.

C. REFERENCES

The following references are herein incorporated by reference.

[1] Holland, T. A.; Mikos, A. G. *J. Controlled Release* 2003, 86, 1-14.
[2] Seeherman, H.; Wozney, *J. M. Cytokine Growth Factor Rev.* 2005, 16, 329-345.
[3] Luginbuehl, V.; Meinel, L.; Merkle, H. P.; Gander, B. *Eur. J. Pharm. Biopharm.* 2004, 58, 197-208.

[4] Andreadis, S. T.; Geer, D. J. *Trends in Biotechnol.* 2006, 24, 331-337.
[5] Panyama, J.; Labhasetwar, V. *Adv. Drug Deliv. Rev.* 2003, 55, 329-347.
[6] Baldwin, S. P.; Saltzman, W. M. *Adv. Drug Deliv. Rev.* 1998, 33, 71-86.
[7] Haesslein A., Hacker M. C., Mikos A. G. *Acta Biomaterialia.* 2008, 4, 1-10.
[8] Anderson, J. M.; Shive, M. S. *Adv. Drug Deliv. Rev.* 1997, 28, 5-24.
[9] Xu, Z. P.; Zeng, Q. H.; Lu, G. Q.; Yu, A. B. *Chem. Eng. Sci.* 2006, 61, 1027-1040.
[10] Kumta P. N., Sfeir C., Lee D. H., Olton D., Choi D. *Acta Biomaterialia.* 2005, 1, 65-83.
[11] Olton, D.; Li, J. H.; Wilson, M. E.; Rogers, T.; Close, J.; Huang, L.; Kumta, P. N.; Sfeir, C. *Biomaterials* 2007, 28, 1267-1279.
[12] Schmidt, S. M.; McDonald, J.; Pineda, E. T.; Verwilst, A. M.; Chen Y. M.; Josephs R.; Ostafin A. E. *Microporous Mesoporous Mater.* 2006, 94, 330-338.
[13] Schmidt H. T.; Gray B. L.; Wingert P. A.; Ostafin A. E. *Chem. Mater.* 2004, 16, 4942-4947.
[14] Xia, W.; Chang, J. *J. Controlled Release* 2006, 110, 522-530.
[15] Barbe, C.; Bartlett, J.; Kong, L. G.; Finnie, K.; Lin, H. Q.; Larkin, M.; Calleja, S.; Bush, A.; Calleja, G. *Adv. Mater.* 2004, 16, 19591966.
[16] Balas F., Manzano M., Colilla M., Vallet-Regi M. *Acta Biomaterialia.* 2008, 4, 514-522.
[17] Blom, E. J.; Klein-Nulend, J.; Wolke, J. G. C.; Kurashina, K.; van Waas, M. A. J.; Burger, E. H. *Biomaterials* 2002, 23, 1261-1268.
[18] Ginebra, M. P.; Traykova, T.; Planell J. A. *Biomaterials* 2006, 27, 2171-2177.
[19] Lee J. Y.; Seol Y. J.; Kim K. H.; Lee, Y. M.; Park, Y. J.; Rhyu, I. C.; Chung, C. P.; Lee, S. J. *Pharm. Res.* 2004, 21, 1790-1796.
[20] Rai, B.; Teoh, S. H.; Hutmacher, D. W.; Cao, T.; Ho, K. H. *Biomaterials* 2005, 26, 3739-3748.
[21] Hartmann, M.; Vinu, A.; Chandrasekar, G. *Chem. Mater.* 2005, 17, 829-833.
[22] Melillo, M.; Gun'ko, V. M.; Tennison, S. R.; Mikhalovska, L. I.; Phillips, G. J.; Davies, J. G.; Lloyd, A. W.; Kozynchenko, O. P.; Malik, D. J.; Streat, M.; Mikhalovsky, S. V. *Langmuir,* 2004, 20, 2837-2851.
[23] Liong M., Lu J., Kovochich M., Xia T., Ruehm S. G., Net A. E., Tamanoi F., Zink J. I. *ACS Nano.* 2008, 2, 889-896.
[24] Vallet-Regi, M.; Rámila, A.; del Real, R. P.; Pérez-Pariente J. *Chem. Mater.* 2001, 13, 308-311.
[25] Slowing I. I.; Trewyn B. G.; Giri S.; Lin V. S. Y. *Adv. Fun. Mater.* 2007, 17, 1225-1236.
[26] Horcajada, P.; Ramila, A.; Boulahya, K.; Callet, J. G.; Vallet-Regi, M. *Solid State Sci.* 2004, 6, 1295-1300.
[27] De Aza, P. N.; Guitian, F.; De Aza, S. *Scripta. Metall. Mater.* 1994, 31, 1001-1005.
[28] De Aza, P. N.; Luklinska, Z. B.; Martinez, A.; Anseau, M. R.; Guitian, F.; De Aza, S. *J. Microsc.* 2000, 197, 60-67.
[29] Liu, X. Y; Ding, C. X.; Wang, Z. Y. *Biomaterials* 2001, 22, 2007-2012.
[30] Xue, W. C.; Liu, X. Y.; Zheng, X. B.; Ding, C. X. *Biomaterials* 2005, 26, 3455-3460.
[31] Lin, K. L.; Zhai, W. Y.; Ni, S. Y.; Chang, J.; Zeng, Y.; Qian W. J. *Ceram. Int.* 2005, 31, 323-326.
[32] Wan, X. H.; Chang, C. K.; Mao, D. L.; Jiang, L.; Li, M. *Mater. Sci. Eng. C* 2005, 25, 455-461.
[33] Casey, W. H.; Westrich, H. R.; Banfield, J. F.; Ferruzzl, G.; Arnold, G. W. *Nature* 1993, 366, 253-256.
[34] Weissbart, E. J.; Rimstidt, J. D. Geochim. *Cosmochim. Acta* 2000, 64, 4007-4016.
[35]. Hartmann, M. *Chem. Mater.* 2005, 17, 4577-4593.
[36] Parida, S. K.; Dash, S.; Patel, S.; Mishra, B. K. *Adv. Colloid Interface Sci.* 2006, 121, 77-110.
[37] Chen J. J., Thomas J. J., Taylor H. F. W., Jennings H. M. *Cem Concr Res.* 2004, 34, 1499-1519.
[38] Hench, L. L. *J. Am. Ceram. Soc.* 1991, 74, 1487.
[39] Kokubo, T.; Kim, H. M.; Kawashita, M. *Biomaterials* 2003, 24, 2161-2175.
[40] Sahai, N.; Tossell, J. A. *J. Phys. Chem. B* 2000, 104, 4322-4341.
[41] Li, P. J.; Zhang, F. P. *J. Non-Cryst. Solids* 1990, 119, 112-118.
[42] Angeli F., Gaillard M., Jollivet P., Charpentier T., *Geochim Cosmochim Acta.* 2006, 70, 2577-2590.

D. CONCLUSION

Mesoporous calcium silicate (e.g., wollastonite) was prepared by acid modification of calcium silicate particles, through the formation of a hydrated silica gel layer having Si—OH functional groups on the surface of the calcium silicate particles. This surface layer had a mesoporous structure having pore diameters around 5 nm (e.g., below 10 nm). Mesoporous calcium silicate particles showed BET specific average surface area as high as 356 m$^2$/g following acid modification at pH 0.5. Protein adsorption studies indicated that mesoporous calcium silicate had a higher capacity for BSA and lysozyme adsorption than unmodified calcium silicate. The release kinetics, discussed above, show that proteins on mesoporous calcium silicate can be released continually over one week, whereas the proteins on unmodified particles showed burst release within a few hours. Methods disclosed herein can be used for synthesis of mesoporous wollastonite that can be used as a carrier for bioactive agents, such as proteins and/or drugs, and for their controlled release during bone regeneration and other biomedical applications.

From the foregoing, it will be appreciated that specific embodiments of the disclosure have been described herein for purposes of illustration, but that various modifications may be made without deviating from the scope of the disclosure. Aspects of the disclosure described in the context of particular embodiments may be combined or eliminated in other embodiments. While features and characteristics associated with certain embodiments of the disclosure have been described in the context of those embodiments, other embodiments may also exhibit such features and characteristics, and not all embodiments need necessarily exhibit such features and characteristics to fall within the scope of the disclosure. The following examples reflect further embodiments of the disclosure.

We claim:
1. A biocompatible composition for controlling release of a bioactive agent, comprising:
    a plurality of calcium silicate (CaSiO$_3$) particles each comprising:
        (i) a crystalline interior portion having a network of covalently bonded silica (SiO$_2$) interrupted and modified by a plurality of calcium cations (Ca$^{2+}$); and

(ii) an exterior surface having a layer of silica gel and having a lower calcium cation concentration than the interior portion, wherein the exterior surface is mesoporous;

a bioactive agent deposited onto the exterior surface or incorporated into the interior portion of each of the calcium silicate particles, wherein the bioactive agent is bonded to the calcium silicate particles in vitro; and a calcium-based ceramic, and wherein the plurality of calcium silicate particles are packed into the calcium-based ceramic.

2. The biocompatible composition of claim 1 wherein the calcium-based ceramic includes at least one of calcium phosphates and calcium sulfates.

3. The biocompatible composition of claim 1 wherein at least one of the calcium silicate particles or the calcium-based ceramic includes at least one dopant, and wherein the dopant includes one or more of a metal salt with metal ions and a metal oxide.

4. The biocompatible composition of claim 3 wherein the dopant includes one or more of Zn2+, Mg2+, Si2+, Na+, K+, Sr2+, Cu2+, Fe3+/Fe2+, Ag+, Ti4+, CO32−, F−, MgO, ZnO, NaF, KF, FeO/Fe2O3, SrO, CuO, SiO2, TiO2, Ag2O, or CaCO3, present in an amount between 0 wt % and about 10 wt %.

5. The biocompatible composition of claim 1 wherein the bioactive agent is a first bioactive agent, and wherein the composition includes a second bioactive agent adsorbed on the calcium silicate particles.

6. A biocompatible composition for controlling release of a bioactive agent, comprising:

a plurality of calcium silicate (CaSiO$_3$) particles each comprising:

(i) a crystalline interior portion having a network of covalently bonded silica (SiO$_2$) interrupted and modified by a plurality of calcium cations (Ca$^{2+}$); and (ii) an exterior surface having a layer of silica gel and having a lower calcium cation concentration than the interior portion;

a bioactive agent deposited onto the exterior surface or incorporated into the interior portion of each of the calcium silicate particles, wherein the bioactive agent is bonded to the calcium silicate particles in vitro and includes at least one of a protein, a polypeptide, a growth factor, a morphogen, an antibiotic, an antimicrobial agent, an osteoporotic drug, or a vitamin; and a calcium-based ceramic mixed with the plurality of calcium silicate particles, the calcium-based ceramic containing calcium phosphates or calcium sulfates.

7. The biocompatible composition of claim 6 wherein the exterior surface includes exposed Si—OH function groups, and wherein the bioactive agent is hydrogen bonded to the exterior surface.

8. The biocompatible composition of claim 6 wherein the plurality of calcium silicate particles do not include calcium cations at the exterior surface.

9. The biocompatible composition of claim 6 wherein a release profile of the bioactive agent includes a burst phase and an extended release phase.

10. The biocompatible composition of claim 9 wherein the extended release phase extends for a plurality of days.

11. The biocompatible composition of claim 6 wherein:
the bioactive agent is a first bioactive agent;
the calcium silicate particles include a first portion of calcium silicate particles having the first bioactive agent adsorbed thereon, the first bioactive agent having a first release profile; and
the calcium silicate particles further include a second portion calcium silicate particles having a second bioactive agent adsorbed thereon, the second bioactive agent having a second release different from the first release profile.

12. The biocompatible composition of claim 6 wherein the calcium silicate particles individually include at least one dopant containing one or more of Zn2+, Mg2+, Si2+, Na+, K+, Sr2+, Cu2+, Fe3+/Fe2+, Ag+, Ti4+, CO32−, F−, MgO, ZnO, NaF, KF, FeO/Fe2O3, SrO, CuO, SiO2, TiO2, Ag2O, or CaCO3.

13. The biocompatible composition of claim 6 wherein the calcium silicate particles individually include at least one dopant containing one or more of Zn2+, Mg2+, Si2+, Na+, K+, Sr2+, Cu2+, Fe3+/Fe2+, Ag+, Ti4+, CO32−, F−, MgO, ZnO, NaF, KF, FeO/Fe2O3, SrO, CuO, SiO2, TiO2, Ag2O, or CaCO3, present in an amount between 0 wt % and about 10 wt %.

14. A biocompatible composition for controlled release of a bioactive agent, the composition comprising:

a plurality of calcium silicate (CaSiO$_3$) particles individually including:

a crystalline interior portion having a network of covalently bonded silica (SiO$_2$) interrupted and modified by a plurality of calcium cations (Ca$^{2+}$); and an exterior surface proximate the interior portion, the exterior surface having a layer of hydrated silica gel with a plurality of Si—OH functional groups;

a bioactive agent deposited onto the exterior surface or incorporated into the interior portion of the individual calcium silicate particles in vitro, wherein the bioactive agent includes at least one of a protein, a polypeptide, a growth factor, a morphogen, an antibiotic, an antimicrobial agent, an osteoporotic drug, or a vitamin; and a calcium-based ceramic mixed with the plurality of calcium silicate particles, the calcium-based ceramic containing calcium phosphates or calcium sulfates, at least one of the calcium silicate particles or the calcium-based ceramic having a dopant containing one or more of Zn$^{2+}$, Mg$^{2+}$, Si$^{2+}$, Na$^+$, K$^+$, Sr$^{2+}$, Cu$^{2+}$, Fe$^{3+}$/Fe$^{2+}$, Ag$^+$, Ti$^{4+}$, CO$_3^{2-}$, F$^-$, MgO, ZnO, NaF, KF, FeO/Fe$_2$O$_3$, SrO, CuO, SiO$_2$, TiO$_2$, Ag$_2$O, or CaCO$_3$, wherein the dopant in the at least one of the calcium silicate particles or the calcium-based ceramic presents in an amount between 0 wt % and about 10 wt %.

15. The biocompatible composition of claim 14 wherein the exterior surface has a calcium cation concentration lower than that of the crystalline interior portion of the individual calcium silicate particles.

16. The biocompatible composition of claim 14 wherein the exterior surface has a calcium cation concentration lower than that of the crystalline interior portion of the individual calcium silicate particles, and wherein a calcium cation concentration at the exterior surface is generally zero.

17. The biocompatible composition of claim 14 wherein the bioactive agent is hydrogen bonded to the exterior surface of the individual calcium silicate particles.

18. The biocompatible composition of claim 14 wherein:
the crystalline interior portion consists of the network of covalently bonded silica (SiO$_2$) interrupted and modified by a plurality of calcium cations (Ca$^{2+}$); and the exterior surface has a calcium cation concentration lower than that of the crystalline interior portion of the individual calcium silicate particles.

19. The biocompatible composition of claim 14 wherein:

the crystalline interior portion consists of the network of covalently bonded silica ($SiO_2$) interrupted and modified by a plurality of calcium cations ($Ca^{2+}$); and a calcium cation concentration at the exterior surface is generally zero.

* * * * *